(12) United States Patent
Takatsuka et al.

(10) Patent No.: US 8,491,522 B2
(45) Date of Patent: Jul. 23, 2013

(54) COMPUTER CONTROLLED ELECTRIC SYRINGE

(75) Inventors: Minoru Takatsuka, Saitama-ken (JP); Kenichi Nakazato, Saitama-ken (JP)

(73) Assignee: Nippon Shika Yakuhin Co., Ltd., Yamaguchi (JP)

( * ) Notice: Subject to any disclaimer, the term of this patent is extended or adjusted under 35 U.S.C. 154(b) by 397 days.

(21) Appl. No.: 12/785,765

(22) Filed: May 24, 2010

(65) Prior Publication Data
US 2011/0190693 A1      Aug. 4, 2011

(30) Foreign Application Priority Data
Jan. 29, 2010   (JP) ................ P2010-017759

(51) Int. Cl.
  *A61M 31/00*   (2006.01)
  *A61M 37/00*   (2006.01)
(52) U.S. Cl.
  USPC ........................................... 604/67; 604/131
(58) Field of Classification Search
  USPC .......................................................... 604/67
  See application file for complete search history.

(56) References Cited

U.S. PATENT DOCUMENTS

| | | | |
|---|---|---|---|
| 5,968,015 A | 10/1999 | Yamamoto | |
| 6,248,093 B1 * | 6/2001 | Moberg | 604/131 |
| 2002/0049415 A1 | 4/2002 | Fukuda | |
| 2002/0133114 A1 | 9/2002 | Itoh et al. | |
| 2004/0073168 A1 | 4/2004 | Takatsuka et al. | |
| 2005/0143653 A1 | 6/2005 | Fukuda | |
| 2006/0079833 A1 | 4/2006 | Kobayashi | |
| 2007/0112310 A1 | 5/2007 | Lavi et al. | |
| 2008/0287873 A1 * | 11/2008 | Liberatore et al. | 604/131 |
| 2011/0166497 A1 * | 7/2011 | Criado et al. | 604/9 |

FOREIGN PATENT DOCUMENTS

| | | |
|---|---|---|
| EP | 1195172 A2 | 4/2002 |
| EP | 1240913 A2 | 9/2002 |
| EP | 1561949 A1 | 8/2005 |
| JP | 2004-130005 | 4/2004 |
| JP | 2004-516107 | 6/2004 |
| WO | 02/051476 | 7/2002 |
| WO | WO-2009/040603 A1 | 4/2009 |
| WO | WO-2009/081103 A1 | 7/2009 |
| WO | WO-2010/007395 A1 | 1/2010 |

OTHER PUBLICATIONS

Extended European Search Report for Appl. 10005466.7 dated Oct. 5, 2012, 6 pages.

* cited by examiner

*Primary Examiner* — Laura Bouchelle
(74) *Attorney, Agent, or Firm* — Andrew M. Calderon; Roberts Mlotkowski Safran & Cole, P.C.

(57) ABSTRACT

A computer controlled electric syringe includes: a piston unit including a piston being configured to press and move a rubber plug of a cartridge by a second end to discharge a medicinal solution from a cartridge through an injection needle; a ball screw having a screw shaft and a nut portion that is screwed into the screw shaft, the screw shaft being loosely inserted into the hollow portion of the piston through the opening, the nut portion being coupled to the piston; a screw shaft supporting portion rotatably supporting the screw shaft of the ball screw; a rotation preventing portion configured to prevent the nut portion of the ball screw from being rotated; and a piston supporting portion supporting the piston to be movable in an axial direction of the screw shaft along with the nut portion by the rotation of the screw shaft.

20 Claims, 20 Drawing Sheets

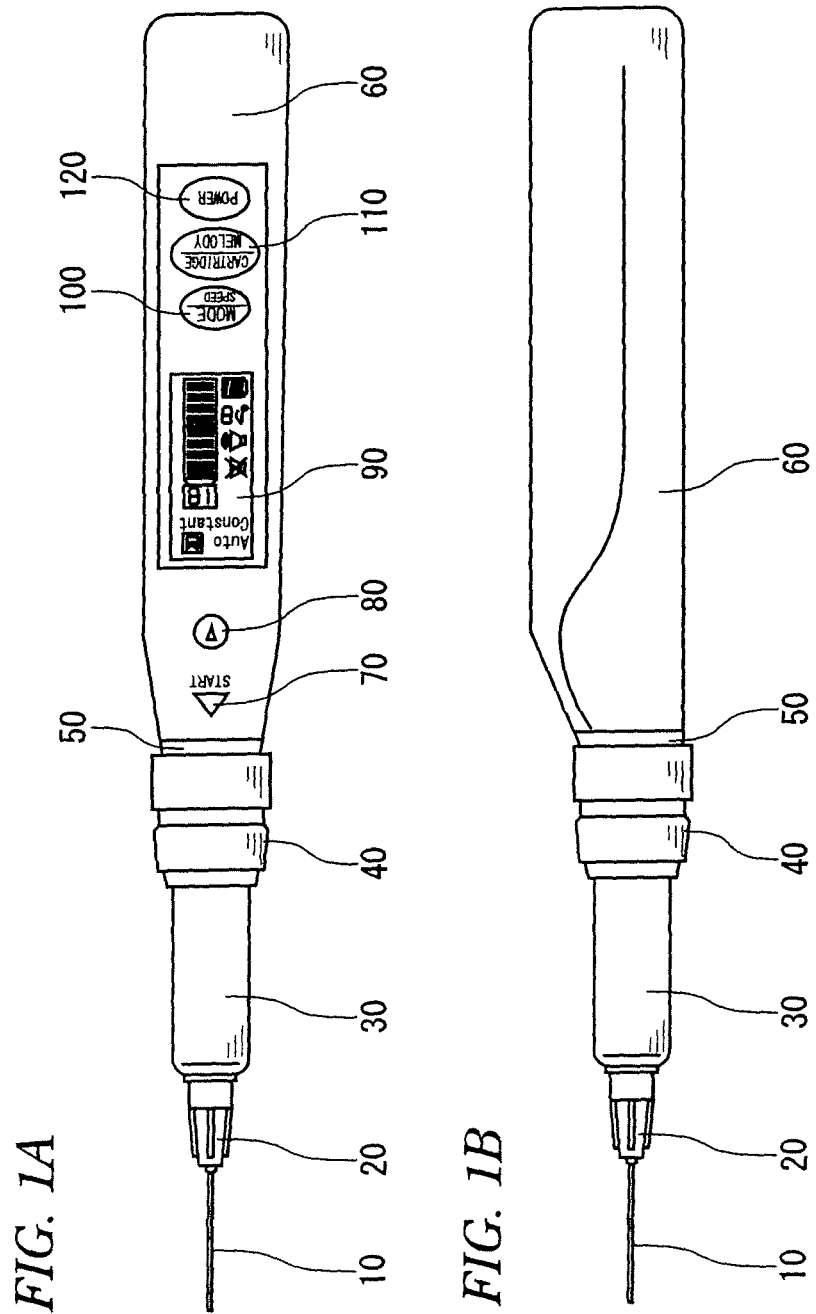

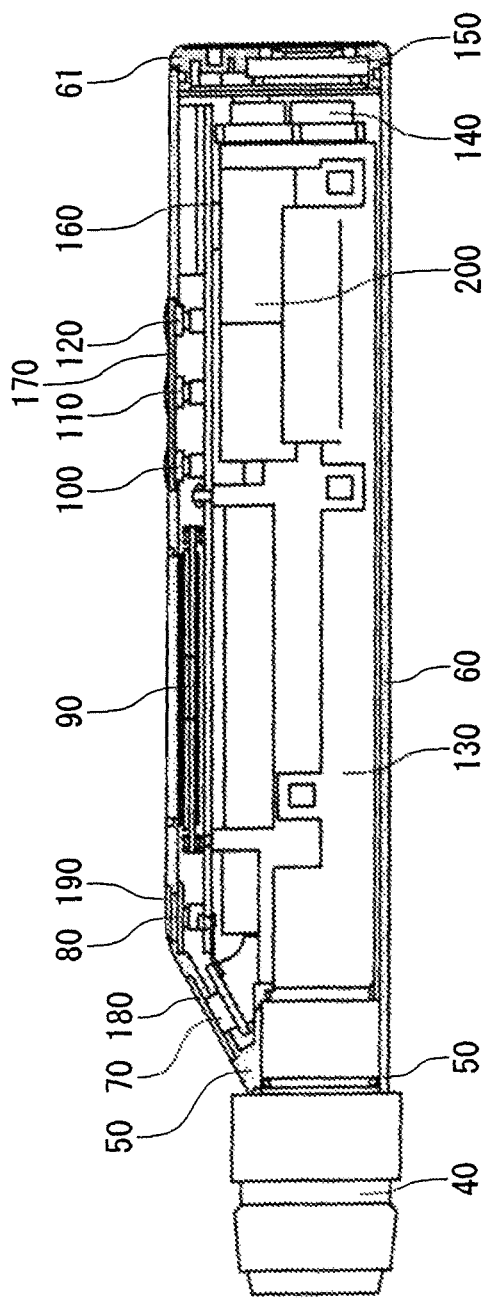
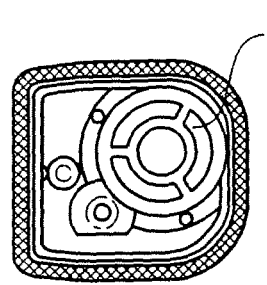
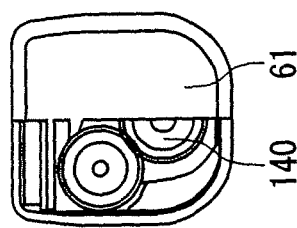

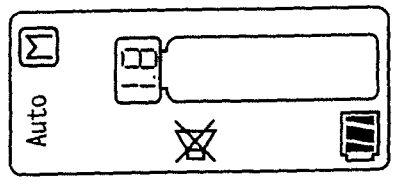
FIG. 20D
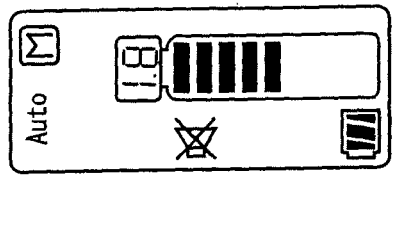
FIG. 20C
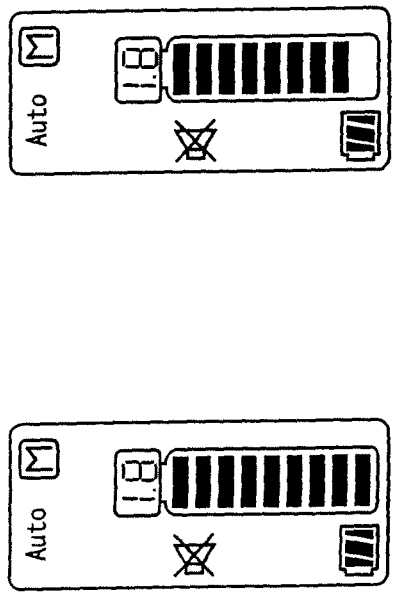
FIG. 20B
FIG. 20A
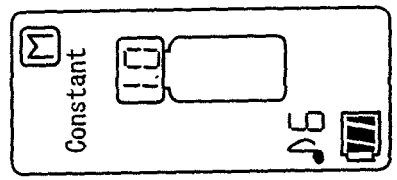
FIG. 20H
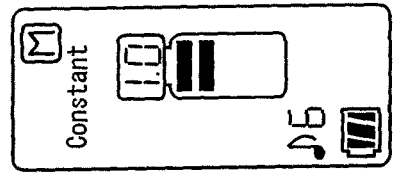
FIG. 20G
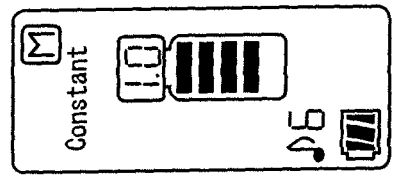
FIG. 20F
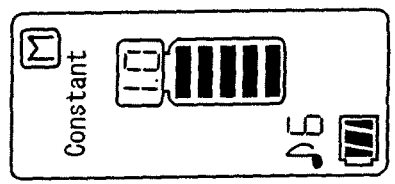
FIG. 20E

COMPUTER CONTROLLED ELECTRIC SYRINGE

CROSS-REFERENCE TO THE RELATED APPLICATION(S)

The present disclosure relates to the subject matters contained in Japanese Patent Application No. 2010-017759 filed on Jan. 29, 2010, which are incorporated herein by reference in its entirety.

BACKGROUND

1. Field

The present invention relates to a computer controlled electric syringe for injecting a medicinal solution to be used in medical treatment or dental treatment.

2. Description of the Related Art

As an instrument which injects a medicinal solution such as an anesthetic, for medical treatment or dental treatment, a manually operated syringe is generally used. In order to alleviate pain using this syringe, it is difficult to perform injection at a low speed and a constant injection speed. Additionally, when a medicinal solution is injected into a hard tissue, large pressing is required, and an operator is forced to make an effort. Moreover, in this case, since the injection speed is sharply changed with fluctuation of the pressing during injection, this can be also a factor which causes pain.

Thus, an electric syringe for injecting a medicinal solution, which is capable of performing injection at a slow injection speed, and also capable of performing injection into a hard tissue while maintaining a constant injection speed is now being widely used.

A conventional configuration that relates to such an electric syringe is disclosed in JP-A-2004-130005 (counterpart U.S. publication is: US 2004/0073168 A1). The publication, JP-A-2004-130005, discloses an electric syringe which is classified into a gun type from its shape, and an electric syringe for a dental treatment anesthetic in which a piston presses and moves a rubber plug of a cartridge in which an anesthetic is enclosed, thereby making the anesthetic flow into a dental injection needle, and makes the anesthetic discharged from a needle tip. In this electric syringe for a dental treatment anesthetic, the injection speed is increased at the beginning of injection, and a constant injection speed is obtained after the lapse of a predetermined period so that pain is kept from occurring.

Another conventional configuration, which is related to the computer controlled electric syringe, is disclosed in JP-T-2004-516107 (counterpart international publication is: WO 02/051476 A1). In JP-T-2004-516107, an electric syringe which is classified into a pen type from its shape is disclosed, and generation of a pain is suppressed because driving is made by the control of an electronic control unit.

The electric syringe for injecting a medicinal solution requires the improvement in usability by realization of a cordless type and miniaturization. Additionally, various questionnaire researches have shown that the pen type which is smaller than the comparatively large-sized gun type has good and preferable usability.

In the electric syringe for a dental treatment anesthetic described in JP-A-2004-130005, although a high torque and a low-speed rotation are realized using a speed-reducing mechanism by a plurality of two-stage gears, there is a problem in that there is no room in internal structure, and additional miniaturization is not easy. A driving unit capable of realizing further miniaturization is desired.

Additionally, even in the pen type injector described in JP-T-2004-516107, a high torque and a low-speed rotation are realized using a speed-reducing mechanism by a plurality of two-stage gears. However, there is a problem in that a plunger is supported at one supporting portion, and a force is concentrated on this supporting portion where damage easily occurs. A driving unit with a mechanically robust construction is desired.

SUMMARY

One of objects of the present invention is to provide a pen-type small computer controlled electric syringe with reduced weight and improved usability.

According to an aspect of the invention, there is provided a computer controlled electric syringe including: a piston unit including: a piston comprising a first end, a second end and a hollow portion communicating with an opening formed at the first end, the piston being configured to press and move a rubber plug of a cartridge, in which a medicinal solution is enclosed, by the second end to discharge the medicinal solution from the cartridge through an injection needle; a ball screw comprising a screw shaft and a nut portion that is screwed into the screw shaft, the screw shaft being loosely inserted into the hollow portion of the piston through the opening, the nut portion being coupled to the piston; a screw shaft supporting portion rotatably supporting the screw shaft of the ball screw; a rotation preventing portion configured to prevent the nut portion of the ball screw from being rotated; and a piston supporting portion supporting the piston to be movable in an axial direction of the screw shaft along with the nut portion by the rotation of the screw shaft.

BRIEF DESCRIPTION OF THE DRAWINGS

A general configuration that implements the various feature of the invention will be described with reference to the drawings. The drawings and the associated descriptions are provided to illustrate embodiments of the invention and not to limit the scope of the invention.

FIGS. 1A to 1C are explanatory views of the external appearance of a computer controlled electric syringe in the embodiment according to the invention, FIG. 1A is a plan view, FIG. 1B is a side view, and FIG. 1C is a back view.

FIGS. 2A to 2C are internal structural views of the computer controlled electric syringe in the embodiment according to the invention, FIG. 2A is a view showing a side structure, FIG. 2B is a view showing the internal structure when a back cover has been removed, and FIG. 2C is a view showing a speaker when the back cover has been removed.

FIG. 3A is a front view, FIG. 3B is a side view which is a partial section, FIG. 3C is a plan view which is a partial section, and FIG. 3D is a back view.

FIG. 9A is a front view, FIG. 9B is a bottom view, FIG. 9C is a plan view, FIG. 9D is an enlarged view of a male screw portion, and FIG. 9E is a sectional view.

FIG. 10A is a view showing a sectional structure, and FIG. 10B is an explanatory view of an arrangement of first and second light-emitting elements.

FIG. 14A is a view showing a cartridge display of 1.8 mL, FIG. 14B is a view showing a cartridge display of 1.0 mL, and FIG. 14C is a view showing a cartridge display of 1.8 mL.

FIG. 15A is a view showing an auto mode display, FIG. 15B is a view showing a constant mode display, and FIG. 15C is a view showing an auto mode display.

FIG. 16A is an explanatory view of a constant mode, and FIG. 16B is an explanatory view of an auto mode.

FIG. 17A is a view showing the display of an injection speed L in the auto mode, FIG. 17B is a view showing the display of an injection speed M in the auto mode, FIG. 17C is a view showing the display of an injection speed H in the auto mode, FIG. 17D is a view showing the display of an injection speed L in the constant mode, FIG. 17E is a view showing the display of an injection speed M in the constant mode, and FIG. 17F is a view showing the display of an injection speed H in the constant mode.

FIG. 18A is a view showing the display of a voice off mode, FIG. 18B is a view showing the display of a buzzer mode, FIG. 18C is a view showing the display of a melody 1 mode, FIG. 18D is a view showing the display of a melody 2 mode, and FIG. 18E is a view showing the display of a melody 6 mode.

FIGS. 20A to 20H are explanatory views of the information display of the computer controlled electric syringe in the embodiment according to the invention, FIG. 20A is an explanatory view of a bar display at the beginning of injection in the auto mode, FIG. 20B is an explanatory view of a bar display during the injection in the auto mode, FIG. 20C is an explanatory view of a bar display during the injection in the auto mode, FIG. 20D is an explanatory view of a bar display at the end of the injection in the auto mode, FIG. 20E is an explanatory view of a bar display at the beginning of injection in the constant mode, FIG. 20F is an explanatory view of a bar display during the injection in the constant mode, FIG. 20G is an explanatory view of a bar display during the injection in the constant mode, and FIG. 20H is an explanatory view of a bar display at the end of the injection in the constant mode.

DETAILED DESCRIPTION OF THE EMBODIMENTS

Figure 3C:
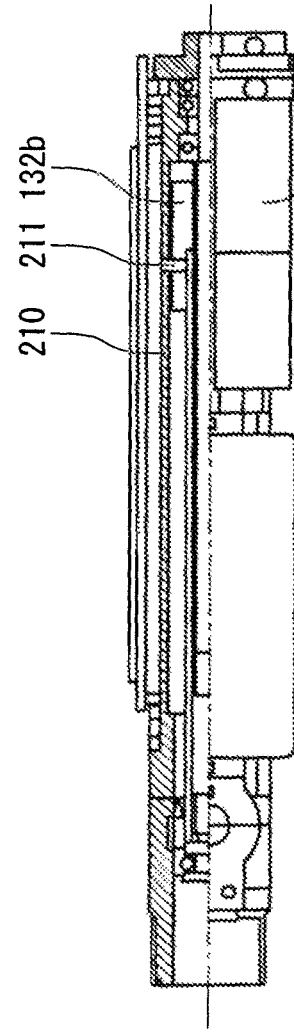
FIGS. 3A to 3D are internal structural views when a body cover of the computer controlled electric syringe in the embodiment according to the invention has been removed.
Figure 3D:
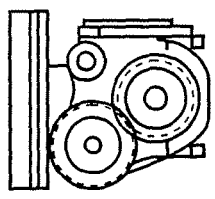

Hereinafter, an embodiment of the invention will be described with reference to the drawings. In the following description, the same or similar components will be denoted by the same reference numerals, and the duplicate description thereof will be omitted. The scope of the claimed invention should not be limited to the examples illustrated in the drawings and those described below.

In the embodiment, description will be made supposing that an anesthetic is used as a medicinal solution, and a computer controlled electric syringe for injecting an anesthetic during dental treatment is used. The computer controlled electric syringe 1, which is a syringe having an external appearance as shown in FIGS. 1A to 1C, has an injection needle 10 (with a needle fixing member 20) attached thereto, and includes a cartridge holder 30, a cartridge holder socket 40, an operation indicator 50, a main case 60, a start switch 70, an aspiration switch 80, an information display 90, a mode/speed setting switch 100, a cartridge/melody setting switch 110, and a power switch 120.

As shown in the internal structural views of FIGS. 2A to 2C in which a body cover is broken away, the computer controlled electric syringe 1 further includes therein a piston unit 130, a drive mechanism 140, a speaker 150, a circuit board 160, a protection seal 170, a start switch protection seal 180, an aspiration switch protection seal 190, and a drive motor 200.

As shown in the internal structural views of FIGS. 3A to 3D except the body cover, the computer controlled electric syringe 1 further includes therein a stroke sensor 210 and a reinforcing ring 220.

Figure 4:
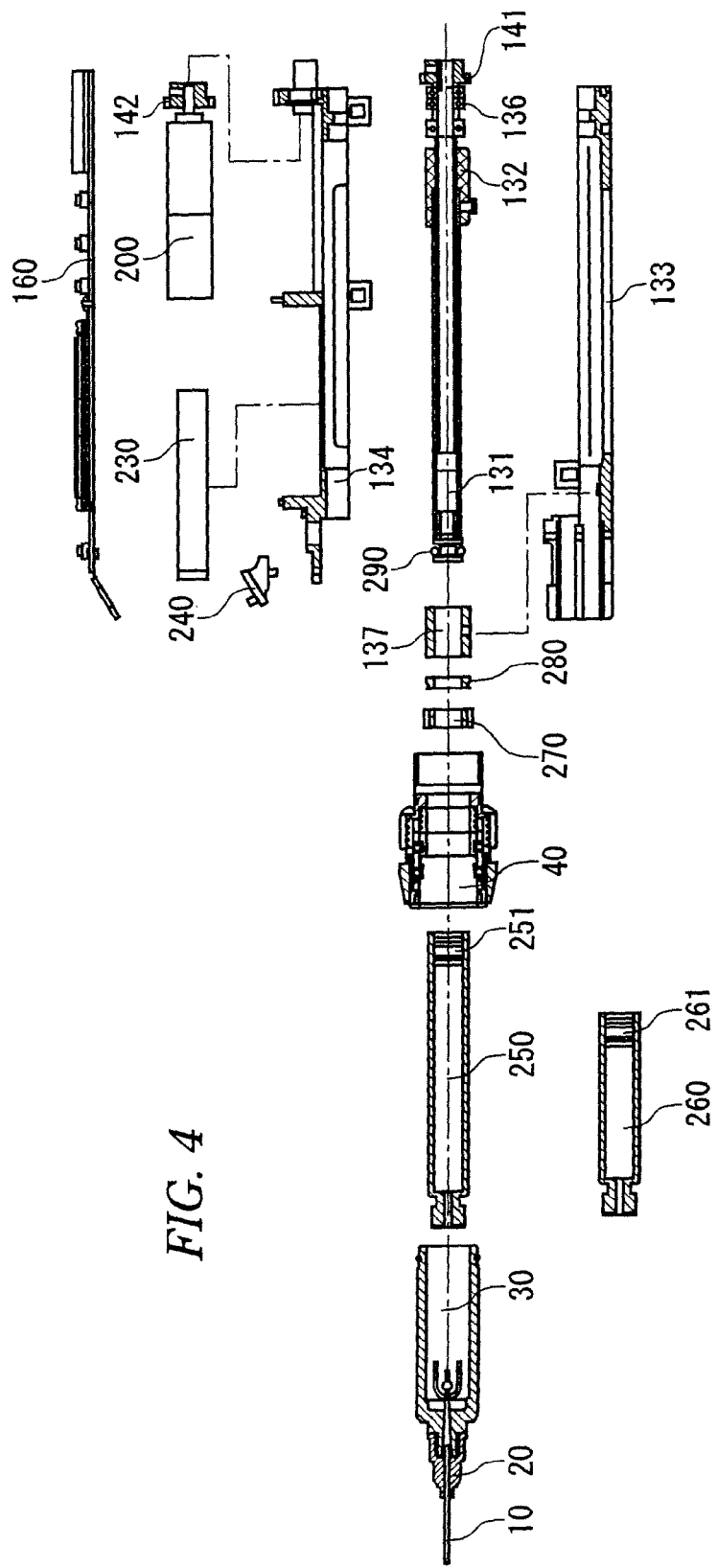
FIG. 4 is a disassembling and assembling view of the computer controlled electric syringe in the embodiment according to the invention.

As shown in a disassembled structural view of FIG. 4, the computer controlled electric syringe 1 further includes therein a battery 230, a condensing body 240, a cartridge (for example, 1.8 mL) 250, a cartridge (for example, 1.0 mL) 260, a packing receptacle 270, packing 280, and an O-ring 290.

Figure 5:
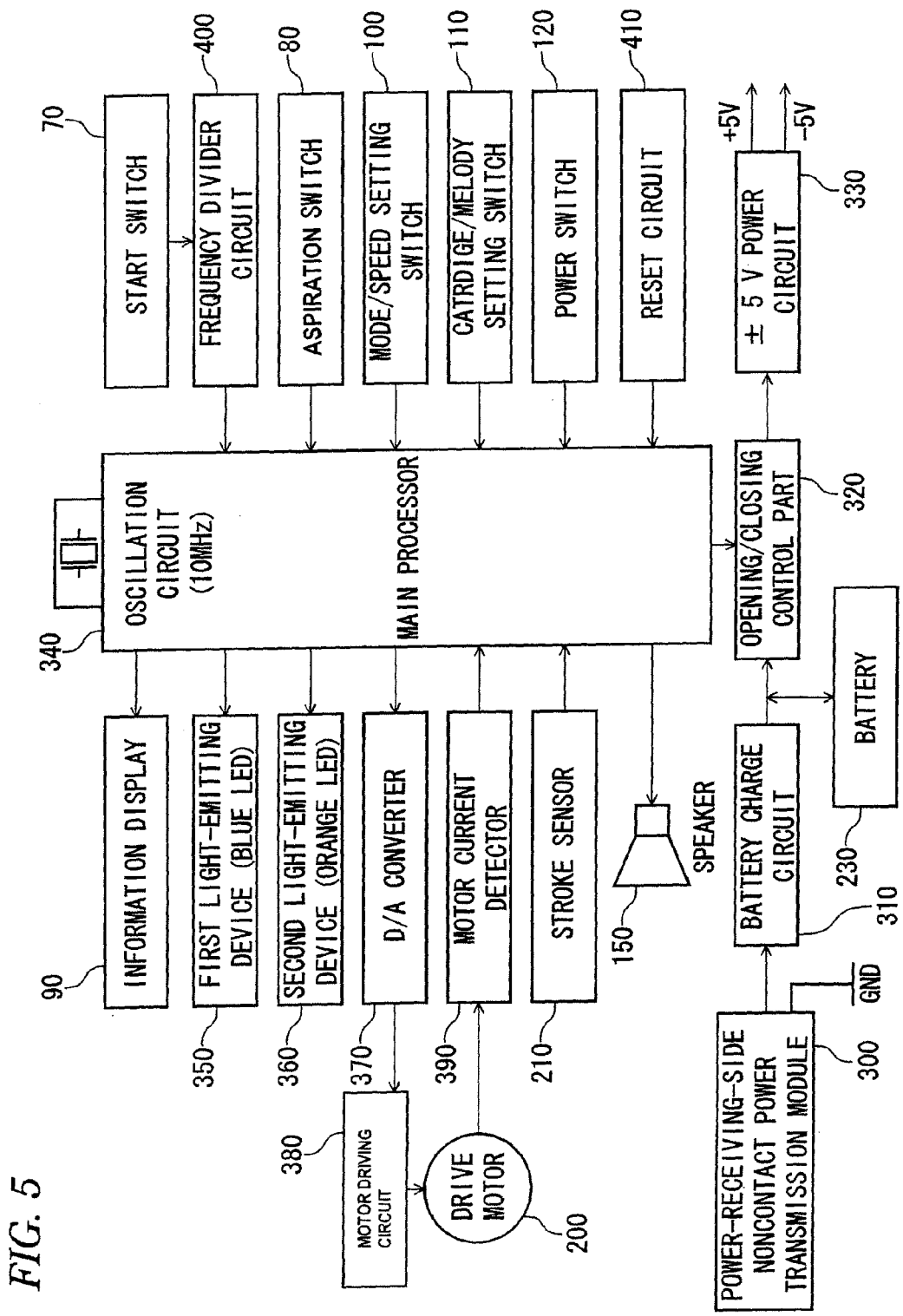
FIG. 5 is a circuit block diagram of the computer controlled electric syringe in the embodiment according to the invention.

As shown in a circuit block diagram of FIG. 5, the computer controlled electric syringe 1 includes a power-receiving-side noncontact power transmission module 300, a battery charge circuit 310, a battery 230, an opening/closing control part 320, an ±5 V power circuit 330, a main processor 340, a first light-emitting device 350, the second light-emitting device 360, the D/A converter 370, the motor driving circuit 380, the drive motor 200, the motor current detector 390, a stroke sensor 210, a speaker 150, a start switch 70, a frequency divider circuit 400, an aspiration switch 80, a mode/speed setting switch 100, a cartridge/melody setting switch 110, a power switch 120, and a reset circuit 410.

Figure 6:
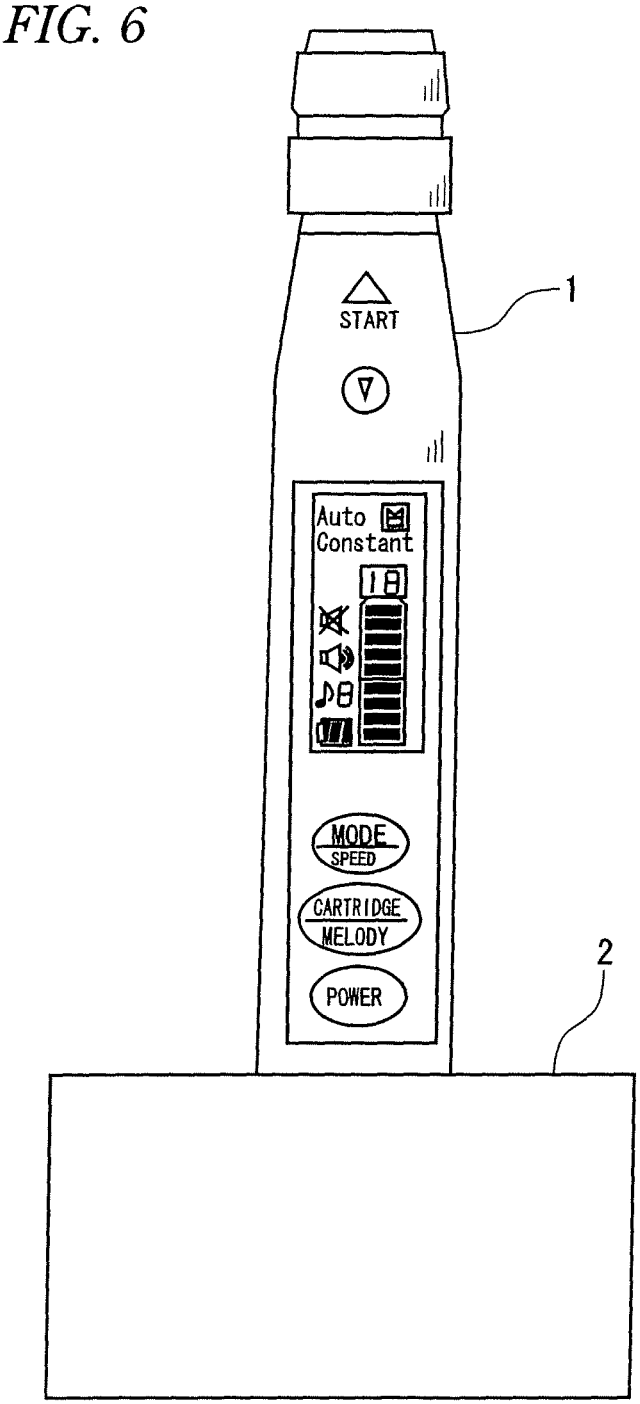
FIG. 6 is an explanatory view of a charge state of the computer controlled electric syringe in the embodiment according to the invention.

As shown in FIG. 6, the computer controlled electric syringe 1 is placed on the battery charger 2 where charge is performed.

Figure 7:
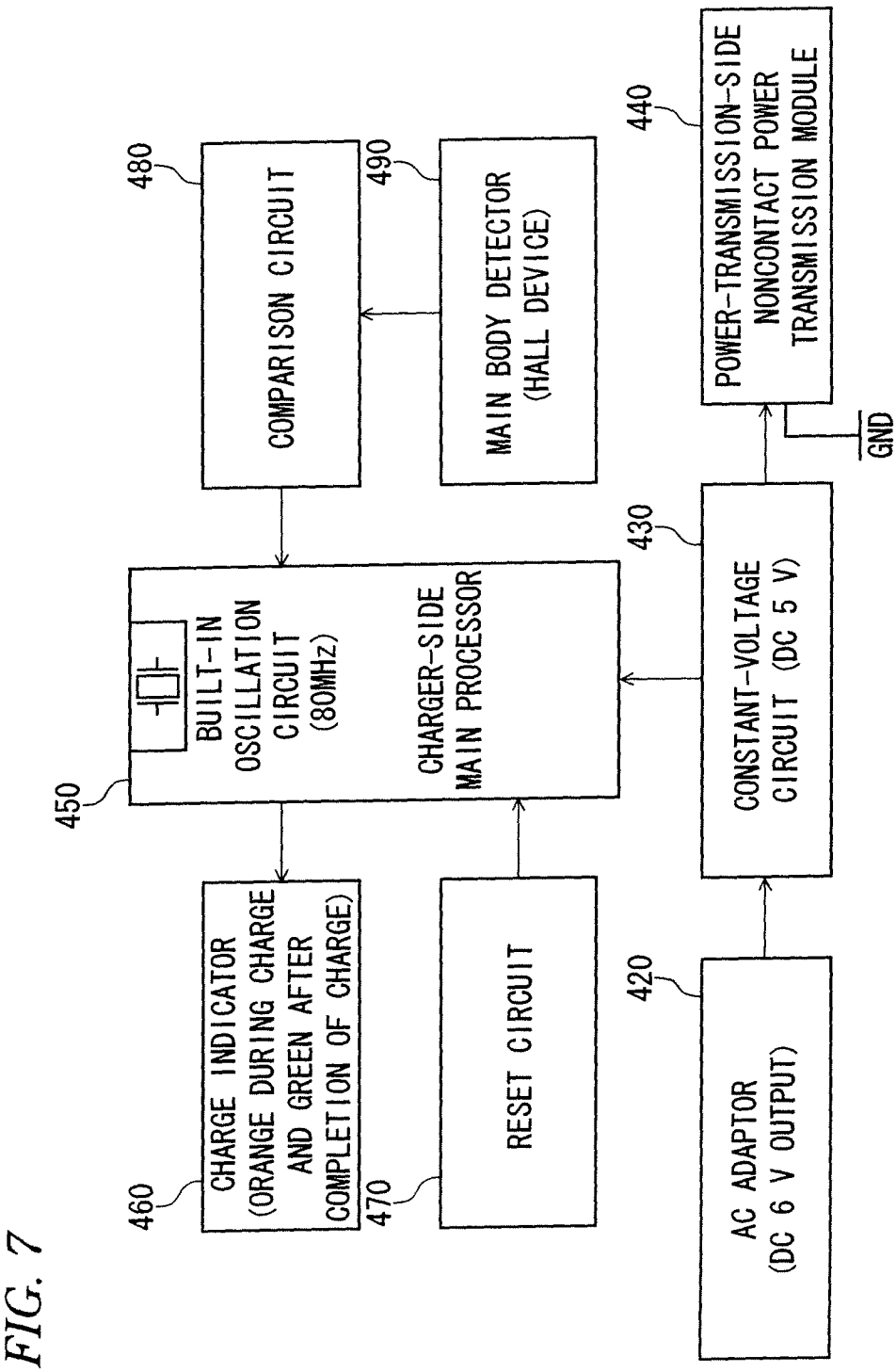
FIG. 7 is a circuit block diagram of a battery charger used for the computer controlled electric syringe in the embodiment according to the invention.

As shown in the circuit block diagram of FIG. 7, the battery charger 2 includes an AC adaptor (DC 6 V output) 420, a constant-voltage circuit (DC 5 V) 430, a power-transmission-side noncontact power transmission module 440, a charger-side main processor 450, a charge indicator 460, a reset circuit 470, a comparison circuit 480, and a main body detector (Hall device) 490.

The injection needle 10 is a hollow needle body as widely known, and is attached to the tip of the computer controlled electric syringe 1 as shown in FIGS. 1A to 1B. The other end of the injection needle 10 reaches the cartridge 250 or 260, and a medicinal solution in the cartridge 250 or 260 flows therethrough. The needle fixing member 20 connects and fixes the cartridge holder 30 to the injection needle 10.

A female screw portion of the needle fixing member 20 is screwed, fastened and fixed to the male screw portion at the cartridge holder 30.

Figure 8:
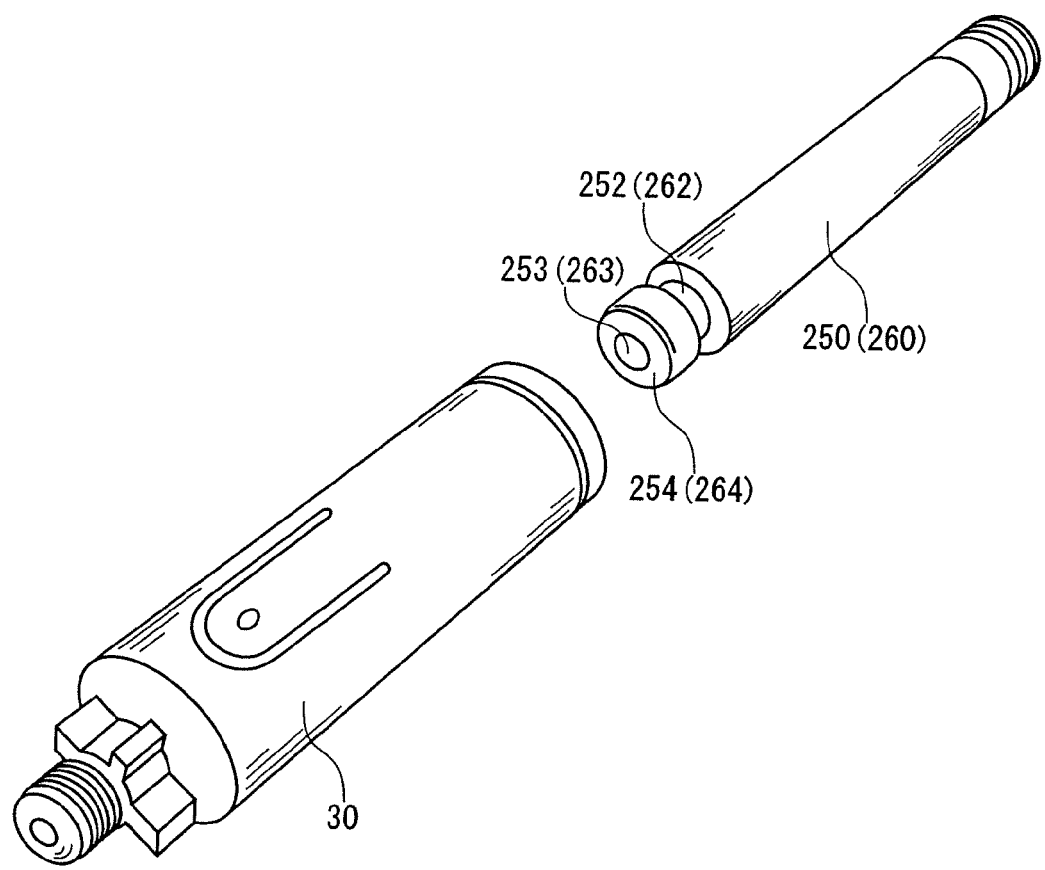
FIG. 8 is an explanatory view of a cartridge and a cartridge holder.
Figure 9C:
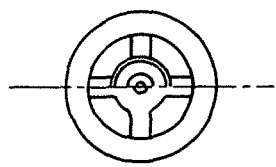
FIGS. 9A to 9E are structural views of a cartridge holder.
Figure 9D:
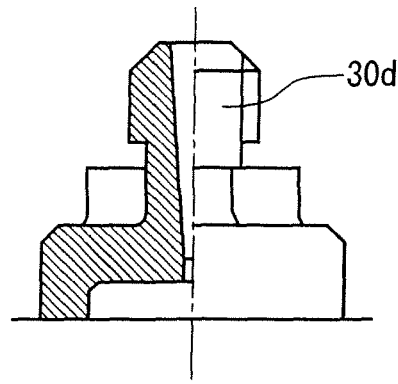
Figure 9A:
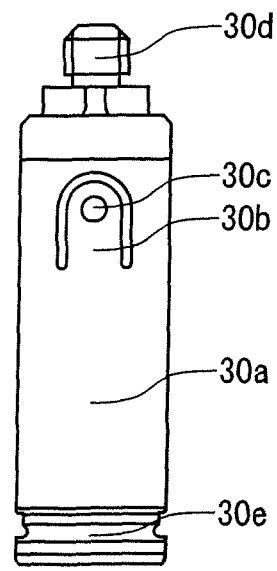
Figure 9E:
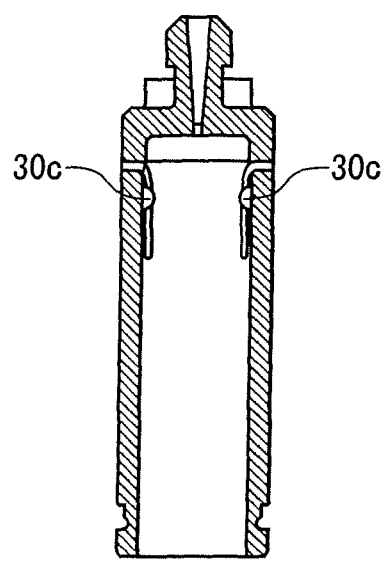
Figure 9B:
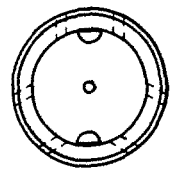

As shown in FIGS. 4 and 8, a cartridge is loaded into the cartridge holder 30. Here, for dental treatment anesthetics, currently, two types of cartridges with different lengths including, for example, the cartridge 250 for 1.8 ml, and the cartridge 260 for 1.0 ml exists. The cartridge holder 30 is constructed so that two types of cartridge are loaded thereinto, and although described later, a piston pushes out a rubber plug of a cartridge so as to push out an anesthetic in the cartridge.

In addition, the cartridge is not limited to those for 1.8 ml and 1.0 ml. For example, it is possible to adopt cartridges which are newly selected later, cartridges for 1.6 ml. Concrete numeric values, such as the amount of a medicinal solution and length, are suitably changed if necessary.

As shown in FIGS. 9A to 9E, the cartridge holder 30 includes a main body 30a, a side piece portion 30b, a protruding portion 30c, a male screw portion 30d, and a groove portion 30e.

The main body 30a is a cylindrical body, and has a length such that a portion of the long cartridge 250 or 260 protrudes.

The side piece portion 30b has one side connected to the main body 30a, has a cut-in formed therearound, and is configured to be movable in a radial direction. Although the side piece portions 30b are formed in two places in the embodiment, for example, the number of places, such as one place or three places, can be suitably set.

The protruding portion 30c is a member which protrudes inward from the side piece portion 30b and fixes the cartridge 250 or 260. The protruding portion 30c is also formed by the same number as the side piece portions 30b. The male screw portion 30d is screwed, fastened and fixed to the male screw portion of the needle fixing member 20. A groove portion 30e is an annular groove formed at an outer periphery near the opening side.

As shown in FIG. 8, an annular groove 252 is provided in the outer peripheral surface of, for example, the cartridge 250 for 1.8 ml, and an annular groove 262 is provided in the outer peripheral surface of, for example, the cartridge 260 for 1.0 ml. Additionally, a cap 254 (264) covers the periphery of a lid 253 (263), such as rubber, at the tip of the cartridge.

When the cartridge 250 (260) is inserted into the cartridge holder 30, the cap 254 (264) pushes up the protruding portion 30c and the side piece portion 30b to the outer peripheral side, and thereafter, the protruding portion 30c enters and is fixed into the groove 252 (262). The cartridge 250 (260) is fixed to the cartridge holder 30 by such a mechanism, and even if the cartridge 250 (260) is pulled, the cartridge is prevented from easily coming off from the cartridge holder 30.

The cartridge holder socket 40 is constructed so that the cartridge holder 30 is detached and attached. As a protruding portion (not shown) of the cartridge holder socket 40 is inserted into or removed from the groove portion 30e of the cartridge holder 30, attachment and detachment of the cartridge holder 30 is performed.

As shown in FIGS. 1A and 1B, FIG. 2A, and FIG. 10A, the operation indicator 50 is arranged in the foremost place at the injection needle side of the main case 60. The operation indicator 50 is formed in the shape of a one-round ring. Although described later, for example, the operation indicator 50 illuminates in various kinds of color during an injection operation, and an operator's attention is called to the fact of being in operation.

The main case 60 is formed in a tubular shape from a transparent material with high waterproofness. Additionally, the main case is formed so as to be tapered toward the injection needle. A hole for putting a machine into the inside is formed in the back of the main body, and is sealed and fixed by a back cover 61 (refer to FIGS. 2A to 2C). Additionally, holes are also formed in the places where the start switch 70, the aspiration switch 80, the information display 90, the mode/speed setting switch 100, the cartridge/melody setting switch 110, and the power switch 120 are placed. Also, the parts excluding the operation indicator 50 is painted to form a protective painting portion. Since the main case 60 has a tapered shape, the operation indicator 50 is formed as a ring-shaped display part which is smaller compared to the back of the main body which has the greatest thickness of the main case 60.

Figure 11:
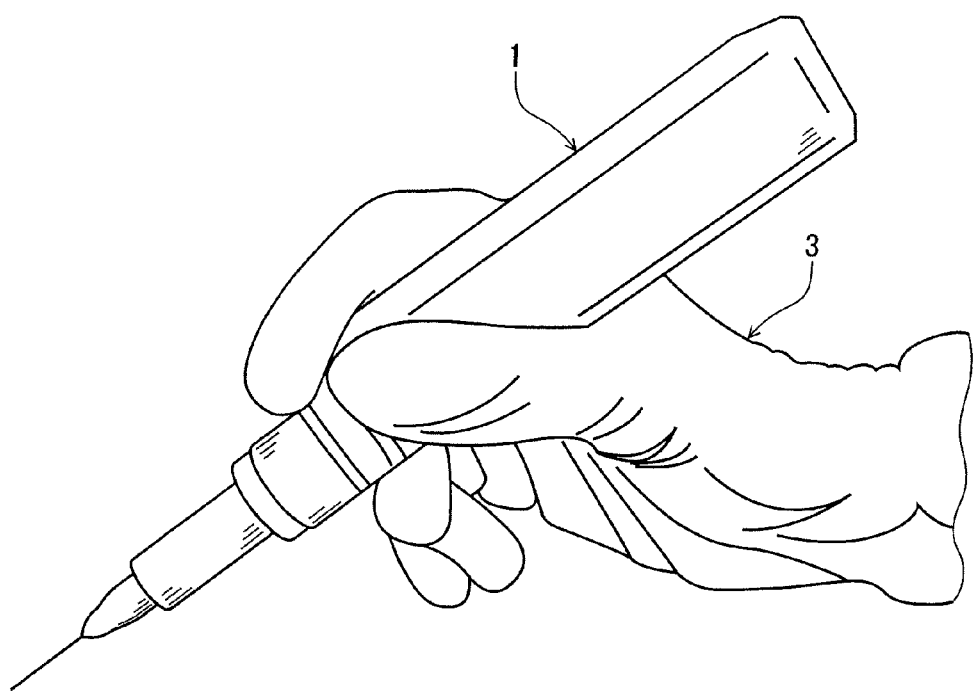
FIG. 11 is a view showing a usage state of the computer controlled electric syringe in the embodiment according to the invention.

As shown in FIG. 5, the start switch 70 is connected to a main processor 340 via the frequency divider circuit 400, and an input regarding the start of injection is made. As shown in FIG. 2A, the start switch 70 is covered and waterproofed with the start switch protection seal 180. In addition, the start switch 70 is a capacitance-type contact switch which senses the presence or absence of contact with part of a person. In the capacitance-type contact switch, as shown in FIG. 11, the point that on/off can be made even via rubber gloves 3 which are worn during operation is confirmed. By adopting this contact switch, mechanical operation is eliminated, and the generation of vibration, etc. is prevented.

In addition, instead of the capacitance-type contact switch, a start switch 70 may be used as a photo-reflector type contact switch. A window hole of the start switch 70 is shielded with a finger, and an operation input is performed. In this case, the frequency divider circuit 400 becomes unnecessary. As a result, in FIG. 5, the start switch 70 is directly connected to the main processor 340, and an input signal from the start switch 70 is input to the main processor 340. Such a start switch 70 may be adopted.

As shown in FIG. 5, the aspiration switch 80 is connected to the main processor 340 and one input regarding aspiration is made. As shown in FIG. 2A, the aspiration switch 80 is covered and waterproofed by the aspiration switch protection seal 190.

As shown in FIG. 5, the information display 90 is a liquid crystal display to be connected to the main processor 340. Display screens are, for example, as shown in FIGS. 14A to 14C, FIGS. 15A to 15C, etc. As shown in FIG. 2A, the information display 90 is covered and waterproofed by the protection seal 170.

As shown in FIG. 5, the mode/speed setting switch 100 is connected to the main processor 340, and an input regarding mode setting or speed setting is made. As shown in FIG. 2A, the mode/speed setting switch 100 is waterproofed by the protection seal 170.

The cartridge/melody setting switch 110 is a cartridge setting switch of the invention. As shown in FIG. 5, the switch is connected to the main processor 340, and an input regarding cartridge setting or melody setting is made. As shown in FIG. 2A, the cartridge/melody setting switch 110 is waterproofed by the protection seal 170.

As shown in FIG. 5, the power switch 120 is connected to the main processor 340 and an input regarding on/off of a power source is made. As shown in FIG. 2A the power switch 120 is covered and waterproofed by the protection seal 170.

Figure 12:
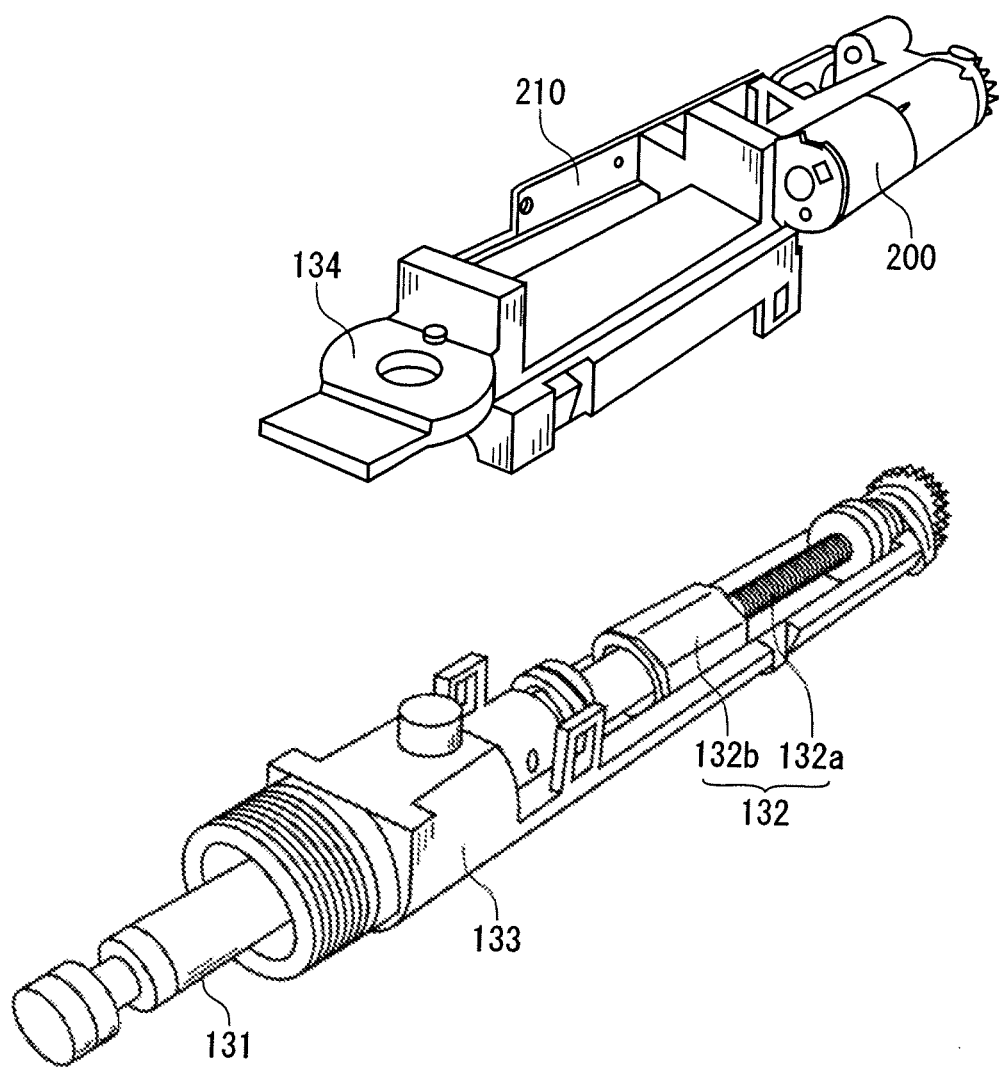
FIG. 12 is a disassembling and assembling view of a piston unit of the computer controlled electric syringe in the embodiment according to the invention.
Figure 13:
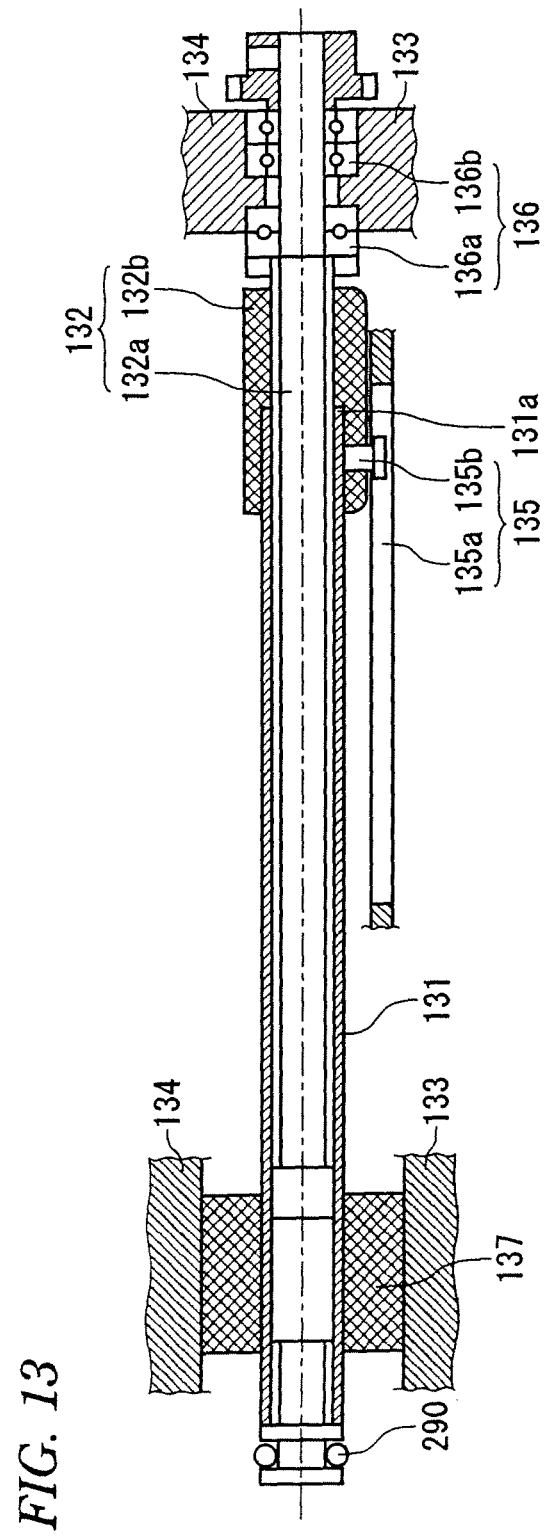
FIG. 13 is a construction view of chief parts of the piston unit.

As shown in FIGS. 2A and 2B, the piston unit 130 is arranged in the main case 60. As FIGS. 3A to 3D, FIG. 4, FIG. 12, and FIG. 13, the piston unit 130 includes a piston 131, a ball screw 132, a bottom base 133, a top base 134, a rotation preventing portion 135, a screw shaft supporting portion 136, and a piston supporting portion 137, and is constructed by the bottom base 133 and the top base 134. As shown in FIGS. 12 and 13, the ball screw 132 includes a screw shaft 132a and a nut portion 132b. The screw shaft supporting portion 136 includes a thrust bearing 136a and a radial bearing 136b. The piston supporting portion 137 is a bearing which supports a piston 131 so that the piston becomes movable in a piston axis direction (thrust direction). The piston is supported so as not to move in a diametrical direction (radial direction) of the piston.

The drive mechanism 140 rotationally drives the screw shaft 132a of the ball screw 132 of the piston unit 130 as shown in FIGS. 2A and 2B, and includes a piston-side gear 141 and a motor-side gear 142 which engage with each other as shown in FIGS. 2B and 4. Additionally, the piston-side gear 141 is fixed to the screw shaft 132a, and the motor-side gear 142 is fixed to a rotary shaft of the drive motor 200.

As shown in FIG. 5, the speaker 150 is connected to the main processor 340. As shown in FIG. 2C, the speaker 150 is arranged near the back of the back cover 61.

As shown in the circuit block diagram of FIG. 5, the power-receiving-side noncontact power transmission module 300, the battery charge circuit 310, the opening/closing control part 320, the ±5 V power circuit 330, the main processor 340, the information display 90, the first light-emitting device 350, the second light-emitting device 360, the D/A converter 370, the motor driving circuit 380, the motor current detector 390, the start switch 70, the frequency divider circuit 400, the aspiration switch 80, the mode/speed setting switch 100, the cartridge/melody setting switch 110, the power switch 120, and the reset circuit 410 are loaded on the circuit board 160, thereby forming a circuit.

As shown in FIG. 2A, the protection seal 170 is provided so as to cover the information display 90, the mode/speed setting switch 100, the cartridge/melody setting switch 110, and the power switch 120, and performs waterproofing.

As shown in FIG. 2A, the start switch protection seal 180 is provided so as to cover the start switch 70, and performs waterproofing.

As shown in FIG. 2A, the aspiration switch protection seal 190 is provided so as to cover the aspiration switch 80, and performs waterproofing.

As shown in FIG. 3C, the drive motor 200 is fixed to a side portion of the piston unit 130, and as shown in FIG. 4, the motor-side gear 142 is pivotally supported and fixed to a driving shaft. As shown in FIG. 5, the drive motor 200 is connected to the motor driving circuit 380, and is rotationally driven.

As shown in FIG. 3C, the stroke sensor 210 is fixed to a side portion of the piston unit 130, and a sensor slider 211 is fixed to the nut portion 132b of the ball screw 132. Since a position detection signal output from the stroke sensor 210 changes according to the movement of the nut portion 132b, positioning can be made using this detection value.

Figure 3B:
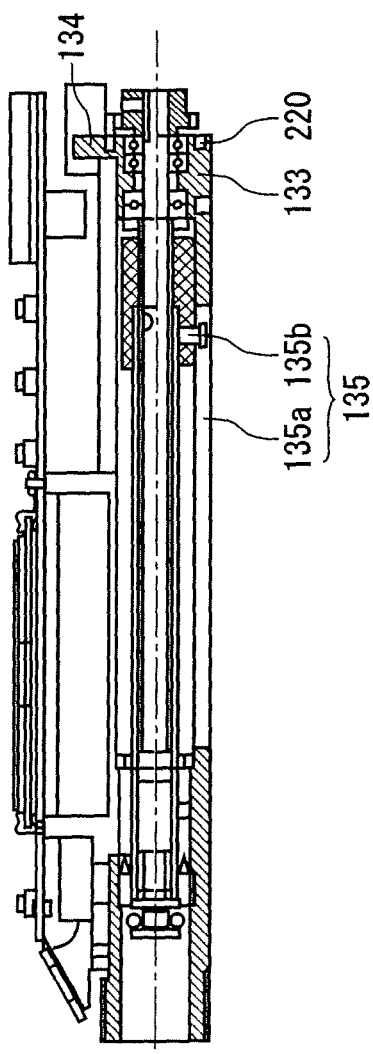

As shown in FIG. 3B, the reinforcing ring 220 is fitted into a groove portion which is formed when the bottom base 133 and the top base 134 are assembled together, and firmly fixes the bottom base 133 and the top base 134.

The battery 230 is connected to the battery charge circuit 310 and the opening/closing control part 320 as shown in FIG. 5, and is fixed to the inside of the groove of the piston unit 130 as shown in FIG. 4. The battery 230 has a charging function, and supplies electric power to respective parts in use.

As shown in FIG. 4, the condensing body 240 is fixed to the tip of the piston unit 130 at the injection needle side. Although described later, the condensing body has a function of condensing the light emitted from the first light-emitting device 350 and the second light-emitting device 360 to the operation indicator 50.

For example, an anesthetic of 1.8 mL is enclosed in the cartridge (1.8 mL) 250. As shown in FIG. 4, the cartridge (1.8 mL) 250 has a rubber plug 251, and when an injection needle 10 is set and the piston 131 pushes the rubber plug 251, the anesthetic comes out of the injection needle 10 (refer to FIG. 19).

For example, an anesthetic of 1.0 mL is enclosed in the cartridge (1.0 mL) 260. As shown in FIG. 4, the cartridge (1.0 mL) 260 has a rubber plug 261, and when an injection needle 10 is set and the piston 131 pushes the rubber plug 261, the anesthetic comes out of the injection needle 10.

As shown in FIG. 4, the packing receptacle 270 is pressed toward the piston unit 130 by the cartridge holder socket 40, and fixes the packing 280.

The packing 280 abuts on the piston 131, maintains watertight structure, and prevents a situation where water enters the main body.

The O-ring 290 abuts on the inner peripheral surface in the cartridge 250 or 260, when the tip of the piston 131 presses the rubber plug 251 or 261 and enters the cartridge 250 or 260, thereby preventing a medicinal solution to leak out from the piston side when injecting the medicinal solution and enabling aspiration capability.

As shown in FIG. 5, the power-receiving-side noncontact power transmission module 300 is an electric-wave system circuit in a circuit, receives a power signal from the power-transmission-side noncontact power transmission module 440 (refer to FIG. 7) of the battery charger 2, and outputs a power signal.

The battery charge circuit 310 receives the power signal, and supplies electric power to the battery 230. If the charge of the battery 230 is completed, an electric power supply is stopped. The battery 230 charges electric power while the opening/closing control part 320 is OFF (while the battery is placed on the battery charger 2), and supplies electric power to the outside while the opening/closing control part 320 is ON (while the battery is detached from the battery charger 2).

The opening/closing control part 320 is connected to the main processor 340, and opens and closes between the battery 230 and the ±5 V power circuit 330 by opening/closing control.

The ±5 V power circuit 330 supplies electric power from the battery 230 to a ±5 V power source. This ±5 V source is supplied to respective components of a circuit system shown in FIG. 5 for driving and control.

The main processor 340 is an example of the main processor of the invention. As shown in FIG. 5, in the body-side processing part, the information display 90, the first light-emitting device 350, the second light-emitting device 360, the D/A converter 370, the motor current detector 390, the stroke sensor 210, the speaker 150, the opening/closing control part 320, the frequency divider circuit 400 (this is provided only when the start switch 70 is of a capacitance type; however, this is unnecessary when the start switch is of a photo-reflector type), the aspiration switch 80, the mode/speed setting switch 100, the cartridge/melody setting switch 110, the power switch 120, and the reset circuit 410 are connected, and control according to various input is performed. Detailed control will be described later.

The first light-emitting device 350 is, for example, a blue LED. The first light-emitting device 350 is controlled to be ON and OFF by the main processor 340.

The second light-emitting device 360 is, for example, an orange LED. The second light-emitting device 360 is controlled to be ON and OFF by the main processor 340.

Figure 10A:
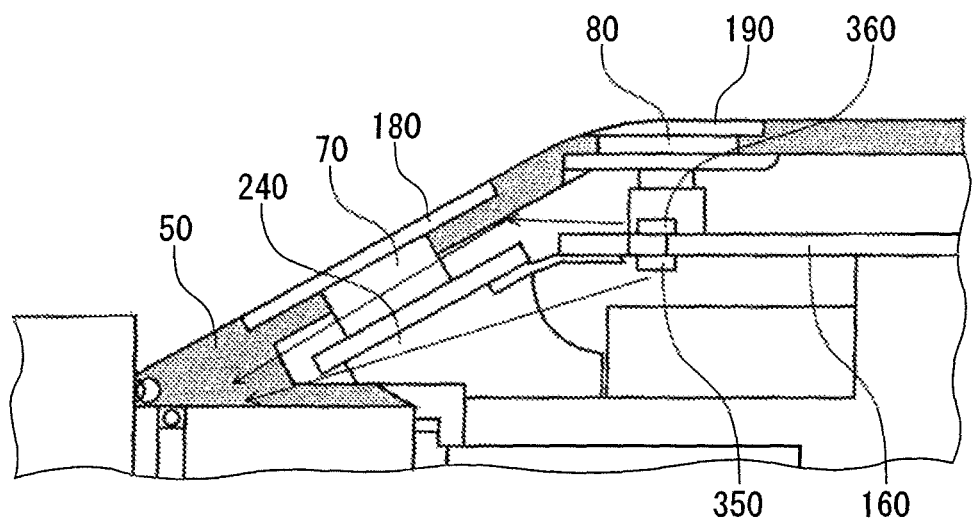
FIGS. 10A to 10B are explanatory views of an operation indicator of the computer controlled electric syringe in the embodiment according to the invention.
Figure 10B:
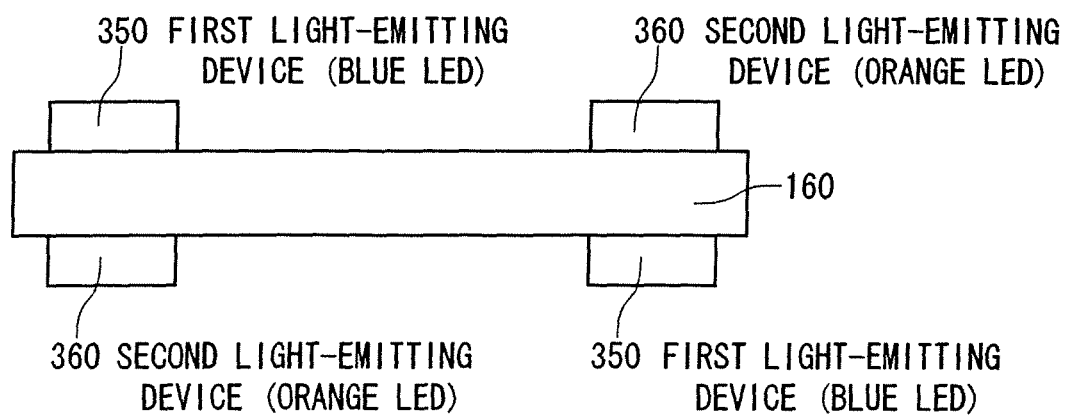

When seen from the front side like FIG. 10B, for example, the first light-emitting device 350 and the second light-emitting device 360 are arranged on the upper and lower sides and on the right and left sides of the circuit board 160.

The D/A converter 370 inputs digital data which controls the rotation of the drive motor 200 from the main processor 340, and converts the digital data into an analog signal.

The motor driving circuit 380 receives the analog signal, and outputs a motor current signal which drives the drive motor 200.

The motor current detector 390 detects the motor current signal input to the drive motor 200, and inputs the motor current signal as a torque signal. The D/A converter 370, the motor driving circuit 380, and the motor current detector 390 constitute a motor controller of the invention.

The frequency divider circuit 400 thins out and outputs a detection signal from the start switch 70, and lengthens intervals for detection, thereby facilitating detection in terms of programs. In addition, the frequency divider circuit 400 is provided only when the start switch 70 is of a capacitance type, and is removed when the start switch is of a photo-reflector type.

The reset circuit 410 detects a supply voltage at the time of power supply or at the time of instantaneous power interruption, and has a function of reliably applying reset to a system. The construction of the computer controlled electric syringe 1 is as described above.

Hereafter, the internal structure of the piston unit which forms the features of the invention will be described. As FIGS. 3A to 3D, FIG. 12, and FIG. 13, the piston unit 130 includes the piston 131, the ball screw 132, the bottom base 133, the top base 134, the rotation preventing portion 135, the screw shaft supporting portion 136, and the piston supporting portion 137.

The piston 131 is a cylindrical body, and has a hollow portion which communicates with an opening of one end. The piston presses and moves the rubber plug 251 or 261 of the cartridge 250 or 260 at the tip portion of the other end.

The ball screw 132 includes the screw shaft 132a of which the outer periphery is threaded, and the nut portion 132b which rotates relative to the screw shaft 132a, and is screwed to the screw shaft so as to move in the direction of the screw shaft. Also, the screw shaft 132a passes through an opening 131a of the piston 131, is loosely inserted into the hollow portion of the piston 131, and is coupled to the nut portion 132b near the opening 131a of the piston 131. That is, the nut portion 132b moves in the direction of the screw shaft, and the piston 131 moves.

The bottom base 133 and the top base 134 fixes the screw shaft supporting portion 136 and the piston supporting portion 137 while sandwiching the portions from above and below. Since the piston unit 130 has a half-split structure through the bottom base 133, and the top base 134, assembling becomes easy.

Figure 3A:
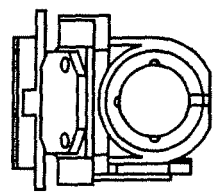

As shown in FIGS. 3A and 3B and FIG. 13, the rotation preventing portion 135 is composed of a protruding portion 135b and a sliding passage 135a. The protruding portion 135b is fixed to the nut portion 132b. The sliding passage 135a is formed in the bottom base 133. The protruding portion 135b is configured so as to move only inside a sliding passage 135a, and such a rotation preventing portion 135 prevents the rotation of the nut portion 132b of the ball screw 132. For this reason, the nut portion 132b and the piston 132 coupled to the nut portion 132b moves only in the axial direction without rotating.

As shown in FIG. 13, the screw shaft supporting portion 136 includes the thrust bearing 136a and the radial bearing 136b, and rotatably supports the screw shaft 132a of the ball screw 132. The thrust bearing 136a bears the force in the direction of the screw shaft which receives especially when the piston 131 presses the rubber plug 251 or 261, and rotatably supports the piston. In particular, since the force in the thrust direction is strong, the force acts so that the bottom base 133 and the top base 134 open. However, since the bottom base and the top base are fixed by the aforementioned reinforcing ring 220, a situation in which the bottom base 133, and the top base 134 open does not occur. Two radial bearings 136b are arranged, and support the screw shaft 132a so that the screw shaft becomes rotatable with respect to the bottom base 133 and the top base 134. The screw shaft supporting portion 136 gives sufficient supporting force by the thrust bearing 136a and the two radial bearings 136b.

The piston supporting portion 137 is a sliding bearing which is sandwiched and fixed by the bottom base 133 and the top base 134. The piston supporting portion 137 does not give a supporting force in the axial direction (the thrust direction) of the screw shaft, but movably supports the piston 131 which moves according to rotation. Additionally, although a sufficient supporting force can be given in the radial direction, since the force which is received in the radial direction is weak, a situation in which the movement of the piston 131 is hindered does not occur.

In such a piston unit 130, the screw shaft 132a in the piston 131 is loosely inserted with a slight gap without touching the inner periphery of the piston 131. Although a strong force is applied to the piston 131 in the axial direction (the thrust direction), since a force is not applied radially (radial direction), the screw shaft 132a in the piston 131 maintains its state, and rotates without touching the inner peripheral surface. Additionally, it is confirmed that operation can be made even if movement is made in the axial direction (the thrust direction) while giving a drag to the piston 131 in the state of being experimentally supported by the screw shaft supporting portion 136 and the piston supporting portion 137.

Such a piston unit 131 has the following advantages. Conventionally, when a ball screw is utilized, it was necessary to support a screw shaft at both ends thereof, and enlargement was not avoided. However, in the present invention, a construction in which one supporting portion of the screw shaft 132a is omitted is adopted. Therefore, one supporting portion is no longer needed, and significant miniaturization is realized. Additionally, since the ball screw 132 is used, a sufficient pressing force can be secured even if a rotative force is small. Therefore, a multi-stage gear speed-reducing mechanism like a conventional technique is no longer required. This also contributes to apparatus miniaturization. Additionally, this leads to miniaturization of a motor and also leads to miniaturization of a battery. In the present invention, these effects are synergistically combined to realize drastic miniaturization and weight reduction, and a cordless and pen-type computer controlled electric syringe 1 is realized.

Hereafter, the operation indicator 50 will be described.

As shown in FIGS. 10A and 10B, the operation indicator 50 is provided at a position adjacent to the cartridge holder socket 40 at the tip of the main case 60. Although the main case 60 is formed of a transparent material as described earlier, and the outer peripheral surface thereof is painted to form a protective painting portion, the operation indicator 50 is formed such that only a ring-like part of the tip thereof becomes transparent without painting. Also the first two light-emitting elements 350 and the second two light-emitting elements 360 are provided on the circuit board 160. As also apparent from FIG. 10B, the first light-emitting device 350 and the second light-emitting device 360 are arranged on the upside of the circuit board 160. The first light-emitting device 350 and the second light-emitting device 360 are arranged on the underside of the circuit board 160. Even when a left end including top and bottom is seen, the first light-emitting device 350 and the second light-emitting device 360 are arranged. Even when a right end including top and bottom is seen, the first light-emitting device 350 and the second light-emitting device 360 are arranged.

For example, when light is emitted in blue and the two first light-emitting elements 350 emit light, light is emitted from right and left and up and down. As shown in FIG. 10A, since an optical path is formed by the condensing body 240 so that light does not dissipate, light is condensed in the direction of the tip, and a blue light is radiated to the outside in the operation indicator 50. It shows that this blue light is irregularly reflected, and is radiated over the whole periphery of the operation indicator 50, and thereby, light is emitted from all directions including the right and left and top and bottom of the operation indicator 50.

Similarly, for example, when light is emitted in orange and the two second light-emitting elements 360 emit light, light is emitted from right and left and top and bottom. As shown in FIG. 10A, since an optical path is formed by the condensing body 240 so that light does not dissipate, light is condensed in the direction of the tip, and an orange light is radiated to the outside in the operation indicator 50. It shows that this orange light is radiated over the whole periphery of the operation indicator 50 by irregular reflection, and thereby, light is emitted from all directions including the right and left and top and bottom of the operation indicator 50.

When both the first light-emitting device 350 and the second light-emitting device 360 are made to emit light, light is condensed by the condensing body 240 and enters the operation indicator 50. However, for example, when blue and orange are mixed, for example, purple is obtained, and consequently, purple light is radiated to the outside of the operation indicator 50. It shows that this purple light is radiated over the whole periphery of the operation indicator 50 by irregular reflection, and thereby, light is emitted from all directions including the right and left and top and bottom of the operation indicator 50.

Such an operation indicator 50 can form a display part with simple construction. Additionally, since the main case 60 is tapered, a small ring-like display part is obtained, and a ring-like display part which was impossible in a normal lamp, etc. is obtained. This display part can be seen from up and down and top and bottom. Additionally, since light is condensed on a small ring, the light is brightly displayed. Additionally, since the two-color light emitting elements are mixed together, three colors can be displayed by the two-color light-emitting elements, which contributes to cost reduction.

In addition, although the case where the luminescent color of the first light-emitting device 350 is a blue color and the luminescent color of the second light-emitting device 360 is an orange color has been described in the embodiment, this embodiment is not intended to be limited to these luminescent colors, and proper luminescent colors can be selected.

Hereafter, the operation about which practical usage of such a computer controlled electric syringe 1 is taken into consideration will be described.

(1) When Charged

As shown in FIG. 6, typically, the computer controlled electric syringe 1 when not used is placed on the battery charger 2 where charge is performed. As shown in FIG. 7, the AC adaptor 420 of the battery charger 2 is connected to a socket to which a commercial power supply is to be supplied, and converts AC 100 V into a voltage of DC 6 V and outputs the converted voltage. The constant-voltage circuit 430 further converts the converted voltage into a voltage of DC 5 V, and outputs the converted voltage to the power-transmission-side noncontact power transmission module 440. The power-transmission-side noncontact power transmission module 440 is a noncontact transmission module, and transmits this voltage of DC 5 V as wireless electric power.

The power-receiving-side noncontact power transmission module 300 shown by FIG. 5 is arranged nearby the power-transmission-side noncontact power transmission module 440 side, and this power-receiving-side noncontact power transmission module 300 receives the electric power which is wirelessly transmitted, and supplies the electric power to the battery charge circuit 310. The battery charge circuit 310 is, for example, a lithium ion charge IC, and charges the battery 230 which is a lithium ion battery. Although the power switch 120 is OFF during this charge, since the opening/closing control part 320 is also OFF in association with the power switch 120, and does not send electric power to a subsequent-stage ±5 V power circuit 330, the whole control system becomes OFF. Accordingly, the battery 230 is charged without consuming power.

In this case, as shown in FIG. 7, when the installation of the computer controlled electric syringe 1 is detected through the comparison circuit 480 by the main body detector (Hall device) 490, it is displayed on a charge indicator 460 that the charger-side main processor 450 is during charge. As a display example, the charge indicator 460 has, for example, a green LED and an orange LED, and performs a display which emits light in orange during charge and emits light in green after the end of charge. In addition, although various display examples can be selected, it is preferable to have a display capable of distinguishing the "during charge" from the "end of charge."

(2) At the Time of Starting/Initializing (Initial Setting) Operation

Hereafter, an actual operation will be described along with operational procedure. In the following description, a case where the main processor controls other components, such as the speaker, the motor controller and the indicators in correspondence with respective switches will be described.

First, when an operator removes the computer controlled electric syringe 1 from the battery charger 2, and pushes the power switch 120 once, the opening/closing control part 320 is turned ON in association with the depression of the power switch 120, electric power is sent to the ±5 V power circuit 330 from the battery 230, and a voltage signal of ±5 V is output. Then, electric power is supplied to respective parts including the main processor 340. Then, when +5 V is also supplied to the reset circuit 410, the reset output from the reset circuit 410 becomes H from L, and the main processor 340 starts the program execution from address 0. An initializing program before a main loop from address 0 is executed. For example, the display of the information display 90 is turned on along with a starting sound from the speaker 150. Additionally, the operation indicator 50 is also turned on, for example, in blue or orange every second. Additionally, the position of the piston 131 moves to and stops at an origin equivalent to a cartridge size which is currently set.

(3) At the Time of Cartridge Switch (Only when Differing from a Previously Used Cartridge)

Figure 14A:
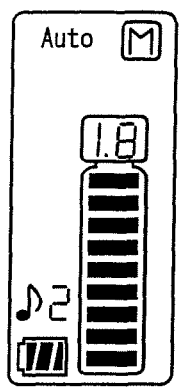
FIGS. 14A to 14C are explanatory views of cartridge switch displays of an information display of the computer controlled electric syringe in the embodiment according to the invention.
Figure 14B:
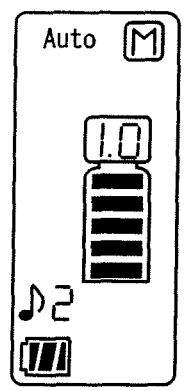
Figure 14C:
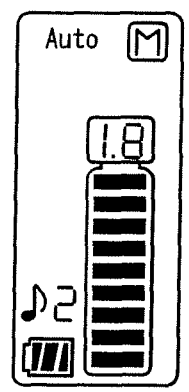

Since switching is alternately made between a cartridge of, for example, 1.8 ml and a cartridge of, for example, 1.0 ml whenever the cartridge/melody setting switch 110 is pushed for long, a cartridge to be used can be set. As shown in FIGS. 14A to 14C, this switching is displayed on the information display 90.

The cartridge of, for example, 1.8 ml is set before switching, and switching to a cartridge of, for example, 1.0 ml from the cartridge of, for example, 1.8 ml shall be made. When the cartridge/melody setting switch 110 is pushed for long over 2 seconds or more, switching of the cartridge size is started. A sound is output simultaneously with the start of switching. Then, the piston 131 moves forward and the position of the piston is automatically adjusted so that a cartridge for, for example, 1.0 ml can be housed. The difference between the position of the tip of a piston for, for example, a 1.8 mL cartridge and the position of the tip of a piston for, for example, a 1.0 mL cartridge is about 21 mm, and the time required for the position adjustment of a piston is, for example, about 10 seconds. In this case, the operation indicator 50 repeats, for example, two blinking at intervals of about 0.8 second-->for example, about turn-off for two seconds-->for example, two blinking at intervals of about 0.8 second, during piston operation. At this time, the display color of the operation indicator 50 becomes a blue color. At the time of the completion of switching, a change to the display of a short cartridge shown in FIG. 14B from the display of a long cartridge shown in FIG. 14A is made along with a switching sound. Every sound is output from the speaker 150.

On the other hand, the cartridge of, for example, 1.0 ml is set before switching, and switching to a cartridge of, for example, 1.8 ml from the cartridge of, for example, 1.0 ml shall be made. When the cartridge/melody setting switch 110 is pushed for long over 2 seconds or more, switching of the cartridge size is started. A sound is output simultaneously with the start of switching. Then, the piston 131 moves back and the position of the piston is automatically adjusted so that a cartridge for, for example, 1.8 ml can be housed. In this case, the operation indicator 50 repeats, for example, two blinking at intervals of about 0.8 second-->for example, about turn-off for two seconds-->for example, two blinking at intervals of about 0.8 second, during piston operation. At this time, the display color of the operation indicator 50 becomes an orange color. At the time of the completion of switching, a change to the display of a long cartridge shown in FIG. 14C from the display of a short cartridge shown in FIG. 14B is made along with a switching sound. Every sound is output from the speaker 150.

In addition, the origin position of a piston in the case of a cartridge of, for example, 1.8 mL coincides with a mechanical origin. Additionally, the origin position of a piston in the case of a cartridge of, for example, 1.0 mL is, for example, about 21 mm away from the origin of a piston in the case of a cartridge of, for example, 1.8 mL in the direction of the tip. For this reason, positioning becomes easy, and movement operation of each origin can be a high-speed operation.

(4) Injection Mode Setting

Figure 15A:
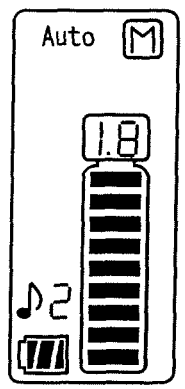
FIGS. 15A to 15C are explanatory views of injection mode displays of the information display of the computer controlled electric syringe in the embodiment according to the invention.
Figure 15B:
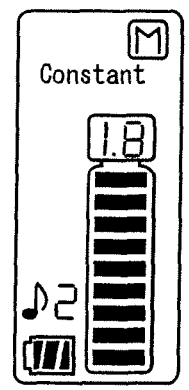
Figure 15C:
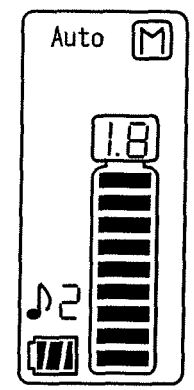

Since switching is alternately made between a constant mode and an auto mode whenever the mode/speed setting switch 100 is pushed for long (for example, about two seconds), an injection mode can be set. As shown in FIGS. 15A to 15C, this switching is displayed on the information display 90.

As shown in 16A, the constant mode is a mode where a constant injection speed is obtained without changing an injection speed. As the injection speed, various kinds of L, M, and H can be selected. As shown in 16B, the auto mode is a mode where the injection speed is increased at the beginning of injection, and a constant injection speed is obtained after the lapse of a predetermined period. As the injection speed, various kinds of L, M, and H can be selected.

The auto mode is set before switching, and switching to the constant mode from the auto mode shall be made. When the mode/speed setting switch 100 is pushed long over 2 seconds or more, switching of the mode is performed. A change to the display of "Constant" as shown in FIG. 15B from the display of "Auto" as shown in FIG. 15A is made along with a switching sound.

On the other hand, the constant mode is set before switching, and switching to the auto mode from the constant mode shall be made. When the mode/speed setting switch 100 is pushed long over 2 seconds or more, switching of the mode is performed. A change to the display of "Auto" as shown in FIG. 15C from the display of "Constant" as shown in FIG. 15B is made along with a switching sound. Every switching sounds which is emitted when a buzzer sound mode and a melody mode is selected is output from the speaker 150.

(5) Injection Speed Setting

Since an injection speed is switched between L (Low: low speed), M (Medium: medium speed), and H (High: high speed) modes by pushing the mode/speed setting switch 100 lightly, the injection speed can be set. In addition, the switching of the injection speed reacts when a finger is separated from the mode/speed setting switch 100. As shown in FIGS. 17A to 17F, this switching is displayed on the information display 90.

Figure 17A:
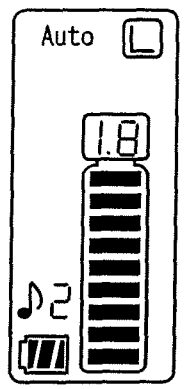
FIGS. 17A to 17F are explanatory views of injection speed displays of the information display of the computer controlled electric syringe in the embodiment according to the invention.
Figure 17B:
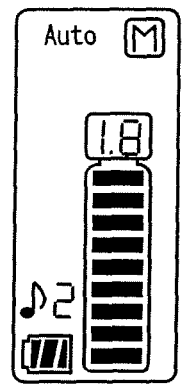

L is set in the auto mode before switching, and switching to M shall be made. When the mode/speed setting switch 100 is lightly pushed, a change to the display of "M" as shown in FIG. 17B from the display of "L" as shown in FIG. 17A is made along with a switching sound.

Figure 17C:
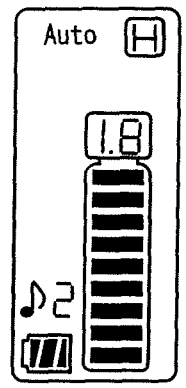

Additionally, M is set before switching, and switching to H shall be made. When the mode/speed setting switch 100 is lightly pushed, a change to the display of "H" as shown in FIG. 17C from the display of "M" as shown in FIG. 17B is made along with a switching sound.

Additionally, H is set before switching, and switching to L shall be made. When the mode/speed setting switch 100 is lightly pushed, a change to the display of "L" as shown in FIG. 17A from the display of "H" as shown in FIG. 17C is made along with a switching sound.

Figure 17D:
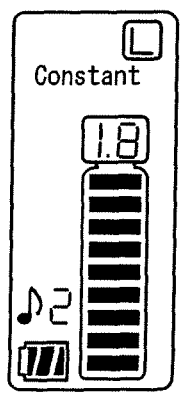
Figure 17E:
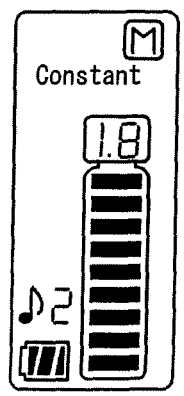
Figure 17F:
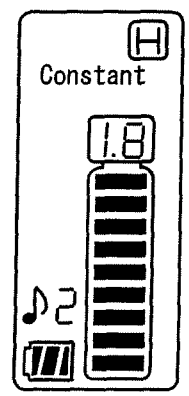

Such switching is also the same in the constant mode as shown in FIGS. 17D, 17E, and 17F, and duplicate description will be omitted. Every switching sounds which is emitted when a buzzer sound mode and a melody mode is selected is output from the speaker 150.

(6) Voice Setting and Melody Setting

Figure 18E:
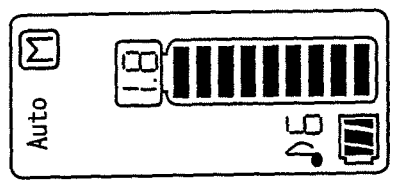
FIGS. 18A to 18E are explanatory views of the display of settings of voice on/off melodies of the information display of the computer controlled electric syringe in the embodiment according to the invention.
Figure 18D:
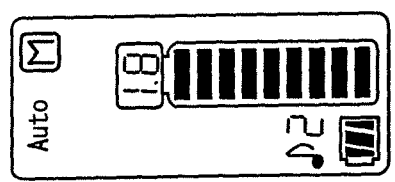
Figure 18C:
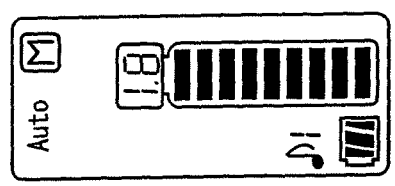
Figure 18B:
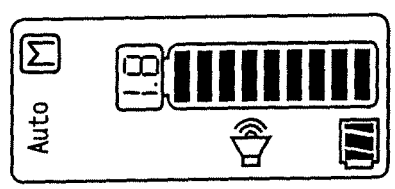
Figure 18A:
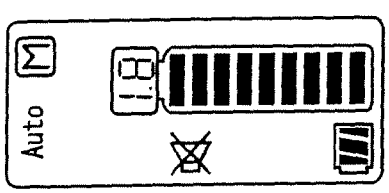

The cartridge/melody setting switch 110 is lightly pushed to set a melody. As shown in FIGS. 18A to 18E, this switching is displayed on the information display 90. Silence and a buzzer sound are also included in the switching of a melody. Whenever the cartridge/melody setting switch is pushed, along with a switching sound, switching is made in the following order: a silence mode (FIG. 18A)-->a buzzer sound mode (FIG. 18B)-->a melody 1 mode (FIG. 18C)-->a melody 2 mode (FIG. 18D)-->a melody n mode (FIG. 18E) (in addition, n is illustratively displayed as 6 in the drawing)-->the silence mode (FIG. 18A). A melody is switched when a finger is removed from the cartridge/melody setting switch 100.

(7) Subsequently, Insert Cartridge into Cartridge Holder.

As shown in FIGS. 4 and 8, when the cartridge 250 or 260 is inserted through an opening of the cartridge holder 30, a tip portion of the cartridge 250 or 260 is brought into contact with and is positioned by a far end in the cartridge holder 30, and the protruding portion 30c is fitted into the groove portion 252 or 262 so as to prevent coming-off.

(8) Mount Cartridge Holder on Main Body.

The cartridge holder 30 to which the cartridge 250 or 260 is fixed is mounted on and fixed to the cartridge holder socket 40 of the main body.

(9) Attach Injection Needle Cartridge Holder.

The injection needle 10 is attached to the tip of the cartridge holder 30 by the needle fixing member 20.

(10) Perform Operation Confirmation with Air-Bleeding

The start switch 70 is lightly touched, and it is confirmed that several drops of medicinal solution come out of the needle tip of the injection needle 10. In this case, the operation indicator 50 blinks (display color: depends on an injection amount) according to an injection speed. Additionally, if an operation confirmation sound is in the melody mode, a melody is played. In addition, the output of silence or a buzzer sound is made depending on setting. Every sound is output from the speaker 150.

(11) Aspiration

Aspiration may be performed by puncturing an affected part with the injection needle 10. Aspiration is performed to confirm that the injection needle 10 does not erroneously enter a blood vessel, and the presence or absence of inflow of blood into a cartridge is visually confirmed. An operator performs aspiration by pushing the aspiration switch 80 lightly. Whenever the aspiration switch 80 is pushed, the piston 131 moves back by a certain distance required for aspiration. When the aspiration switch 80 is pushed, the main processor 340 performs a control so that the motor driving circuit 380 moves back the piston 131 by, for example, about 2 mm at high speed, and then stops the piston. In this case, the presence or absence of inflow of blood into the cartridge 250 or 260 by the negative pressure to a medicinal solution caused with the expansion of the medicinal solution and the rubber plug 251 or 261 is visually confirmed. Additionally, an orange color is displayed on the display part 50 for operational confirmation. As for an operation confirmation sound, when the aspiration switch 80 is pushed, a sound is output from the speaker 150. In addition, when aspiration cannot be made, for example, it is notified that aspiration could not be made such that a sound is produced twice like "ta-ta". In addition, even if the aspiration switch 80 continues to be pushed, the piston 131 does not continue to move back.

(12) Start Injection.

Figure 16A:
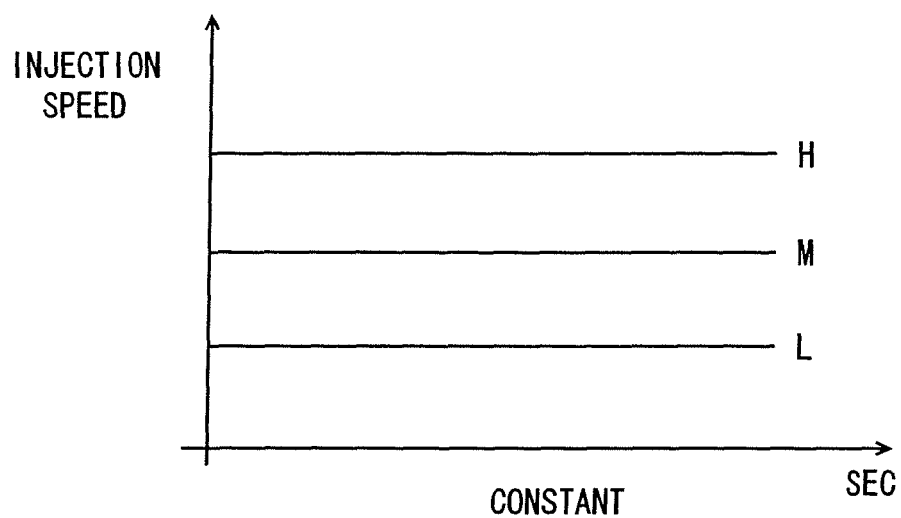
FIGS. 16A and 16B are explanatory views of injection modes and injection speeds.
Figure 16B:
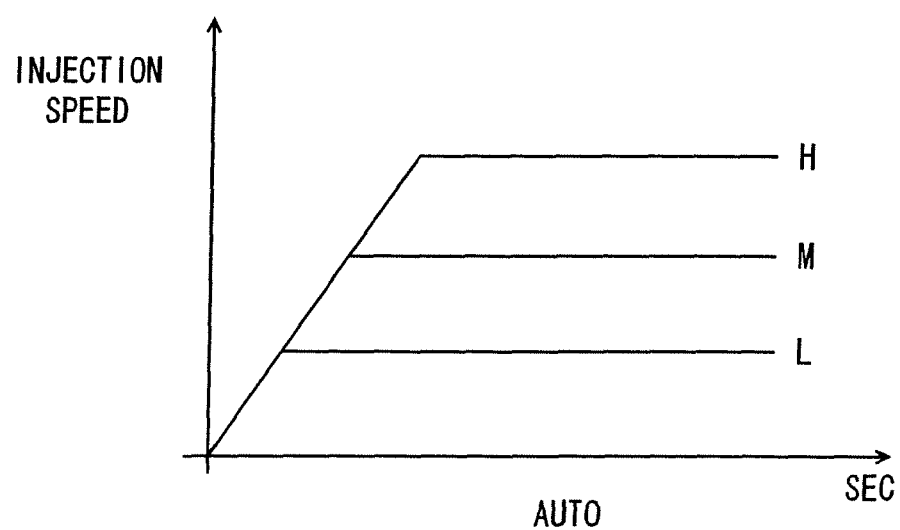
Figure 19:
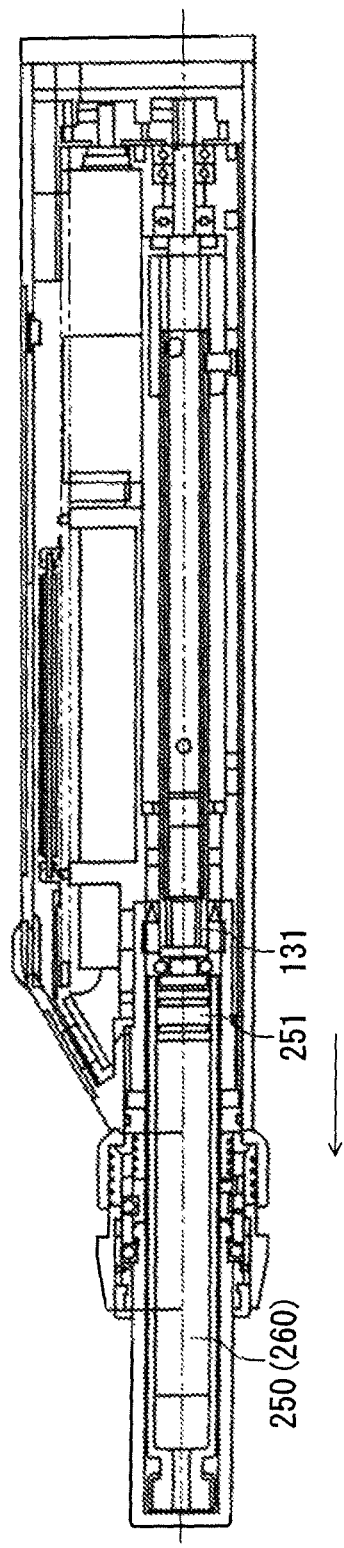
FIG. 19 is a sectional structural view of a usage state of the computer controlled electric syringe in the embodiment according to the invention.

When the start switch 70 is touched lightly, injection is started according to an injection mode or an injection speed which is currently set. As shown in FIG. 19, the piston 131 moves in the direction of an arrow, and the rubber plug 251 or 261 of the cartridge 250 or 260 is pressed at a predetermined injection speed. When the main processor 340 outputs drive data to the D/A converter 370, the drive motor 200 starts rotation via the motor driving circuit 380. Since this rotation operation is a slow-up operation (refer to FIG. 16B) in the auto mode, the drive data which raises a voltage stepwise is input to the D/A converter 370, thereby increasing the rotation of the drive motor 200, and this rotation continues until a prescribed speed is obtained.

The monitoring of the speed is performed by the comparison between the motor speed data prepared on the basis of a detection signal from the stroke sensor 210, and the reference data registered inside the main processor 340.

If reference data>motor speed data, a motor voltage is increased.

If reference data<motor speed data, a motor voltage is reduced.

Also, when the piston 131 continues to move forward and reaches the tip, the main processor 340 stops the drive motor 200 by setting the output of the D/A converter 370 to 0 V.

Since the stroke sensor 210 is directly connected to the piston 131 during driving, the current position can be monitored. The main processor 340 displays a value equivalent to the position of the piston 131 with a bar graph of the information display 90.

As for a liquid crystal display during operation, as shown in FIGS. 20A to 20D, the following bar displays are performed in the auto mode and in a 1.8 mL cartridge. Although all the bars are displayed at the beginning of injection as shown in FIG. 20A, the bars displayed decrease as injection proceeds as shown in FIGS. 20B and 20C, and eventually, all the bars are not displayed and it is displayed that there is no residual amount as shown in FIG. 20D.

As shown in FIGS. 20E to 20H, the following bar displays are performed in the constant mode and in a 1.0 mL cartridge. Although the bars are displayed at the beginning of injection as shown in FIG. 20E, the bars displayed decrease as injection proceeds as shown in FIGS. 20F and 20G, and eventually, all the bars are not displayed and it is displayed that there is no residual amount as shown in FIG. 20H.

Additionally, the operation indicator 50 blinks according to an injection speed during driving. Thereby, the injection speed can be confirmed. Additionally, color changes (examples: for example, 0 to 0.6 mL-->for example blue; for example, 0.6 to 1.2 mL-->for example, orange; and for example, 1.2 to 1.8 mL-->for example, purple) according to the lighting color or injection amount in the display part 50 for operational confirmation. For example, in the case of blue, only two first light-emitting elements 350 emit light. For example, in the case of orange, only two second light-emitting elements 360 emit light. For example, in the case of purple, the two first light-emitting elements 350 and the two second light-emitting elements 360 emit light. Since color changes with an injection amount in this way, the injection amount can be confirmed.

Moreover, "during injection" can be confirmed by blinking or color. Since the blinking or color is near an injection needle, the blinking or color easily come within an operator's field of view, and "during injection" is reliably recognized.

The operation confirmation sound is as follows in the silence mode.

Start sound-->No; During injection-->No; Stop sound-->No; and Ct. End-->Yes

The operation confirmation sound is as follows in the buzzer sound mode.

Start sound-->Yes; During injection-->Yes; Stop sound-->Yes; and Ct. End-->Yes

The operation confirmation sound is as follows in the melody mode.

Start sound-->No (Melody); During injection-->No (Melody); Stop sound-->No; and Ct. End-->Yes Every sound is output from the speaker 150.

(13) End Injection

A finger is lifted off the start switch 70 after the end of injection, and injection is ended.

The main processor 340 performs data output of a slow-up voltage to the D/A converter 370, and outputs to the motor driving circuit a signal which returns a piston to an origin position at high speed. 5 seconds after each cartridge is fully pushed, the retreat of a piston begins automatically, and the piston returns to the zero point position of each cartridge.

The operation indicator 50 is turned off.

The operation confirmation sound is as follows.

No sound is output in the silence mode.

A buzzer sound is output in the buzzer sound mode.

A melody stops in the melody mode.

(14) The Cartridge Holder Socket is Operated to Detach the Cartridge Holder from the Main Body. Subsequently, a Cartridge is Detached from a Piston (Only When an Aspiration Rubber is Mounted).

(15) Turn Off the Power and End Operation.

The power switch 120 is pushed long (for example, about 2 seconds) and the power is turned off. The information display 90 is turned off with a confirmation sound, and the piston 131 moves back automatically. The piston returns to the zero point position of each cartridge. In this case, the operation indicator 50 does not blink. Additionally, the operation confirmation sound is as follows No sound is output in the silence mode.

In the buzzer sound mode, a sound is output only when a button is pushed for long.

In the melody mode, a sound is output only when a button is pushed for long.

The operation of the computer controlled electric syringe 1 is as described above.

As described above, the following contrivances have been made in the present invention.

(1) Since the structure in which the ball screw 132 and the piston 131 are integrated, and the movement of the ball screw 132 is directly transmitted to the piston 131 is adopted, shape is made compact.

(2) As the piston unit 130 is half-split and assembled in the axial direction, driving portions are made to have small-sized diameter.

(3) The shape which makes it easy to grasp the grip portion of the main case 60 is obtained by the contrivance of the arrangement of built-in parts.

Although the case where a computer controlled electric syringe is used for injection of an anesthetic at the time of dental treatment has been described in the description of the embodiment, the invention is not intended to be limited to dental treatment, but may be applied to medical treatment of human beings or other animals (beasts, such as a dog, a cat, a cow, and a horse). Moreover, the invention is not intended to be limited to an anesthetic, but a medicinal solution, such as insulin, may be used.

Additionally, as for the start switch 70, a press switch which outputs a detection signal according to the pressed amount may be adopted instead of a contact type switch. It is also preferable that this press switch is a switch which includes a Hall device for detecting a stroke of the pressed amount and outputs a detection signalin accordance with the stroke detected by the Hall device.

Also, the main processor 340 controls the motor controller so as to perform injection at an injection speed according to the detection signal output from the press switch. Thereby, if the injection speed can be controlled according to the pressed amount, it is also possible to cope with a case where an operator controls the injection speed arbitrarily according to a part into which the injection needle is inserted. Such a computer controlled electric syringe may be adopted.

Additionally, a computer controlled electric syringe may be adopted in which an engaging portion is provided at the tip of the piston 131, the main processor 340 outputs drive data to the D/A converter 370 so that, according to the depression of the aspiration switch 80, the tip of the piston 131 is locked to the rubber plug of an empty cartridge, and the rubber plug of the empty cartridge is pulled in with the piston 131, and the function of making a medicinal solution aspirated into the empty cartridge by the negative pressure which is caused with the pull-in of the rubber plug of the empty cartridge is added.

By adding an aspiration function, a medicine can be aspirated into an empty cartridge, and administration of the aspirated medicine becomes possible.

In addition, in this computer controlled electric syringe, various inventions are inherent.

For example, it is necessary to clean the computer controlled electric syringe for the prevention of infection by bacteria and the prevention of contamination of the main body. Therefore, a structure in which cleaning and sterilization are possible by whole washing is desirable. However, a computer controlled electric syringe with a perfect waterproof structure does not exist conventionally, and a computer controlled electric syringe with a perfect waterproof structure is needed. In addition, in a conventional electric syringe in which charge is made by the contact between an electrode and an electrode, a charging terminal is exposed. Therefore, when the terminal portion is soiled, there is a possibility that poor charge may be caused. Thus, the computer controlled electric syringe of the invention includes the following invention which solves such problems.

As described with reference to the embodiment, there is provided a computer controlled electric syringe in which a rubber plug of a cartridge in which a medicinal solution is enclosed is pressed and moved to make a medicinal solution flow into an injection needle and make the medicinal solution discharged from the injection needle. The electric syringe further includes a piston unit; a drive mechanism which transmits a rotative force to the piston unit; a drive motor which transmits a rotative force to the drive mechanism; a motor controller which controls the driving of the drive motor; a stroke sensor which detects the position of the piston of the piston unit; a power supply unit which supplies power to the drive motor, the motor controller, and the stroke sensor; a main processor to which a motor controller, a stroke sensor, and a power supply unit are connected; a main case which covers the piston unit, the drive mechanism, the drive motor, the motor controller, the power supply unit, the stroke sensor, and the main processor; and a cartridge holder socket which is connected to the main case, is provided so that the piston protrudes while maintaining the watertight structure which prevents entrance of water thereinto, and attaches and detaches the cartridge holder into which a cartridge is inserted.

Preferably, in the above computer controlled electric syringe, the power supply unit includes a noncontact power transmission module, a battery charge circuit connected to the noncontact power transmission module, and a battery connected to the battery charge circuit. Electric power is supplied by noncontact from the outside through the noncontact power transmission module, and the battery is charged.

By making the computer controlled electric syringe into a perfect waterproof structure, washing of the main body and sterilization by soaking in a disinfectant become possible, and injection in a cleaner state becomes possible. Additionally, since the noncontact charge type is adopted, there is no exposure of a charging terminal, the poor charge by the soiling of the charging terminal is eliminated, and washing by soaking in a cleaning solution and disinfection by soaking in a disinfectant also become possible.

Additionally, in the conventional technique, the movement of a needle tip in the case of injection causes pain. Therefore, it is desirable that the vibration transmitted to the needle tip at the time of start or stop of injection is small. Since a button-type switch is used in the conventional technique, vibration is transmitted to the needle tip by the pressing of the button. Thus, the computer controlled electric syringe of the invention includes the following invention which solves such problems.

As described with reference to the embodiment, there is provided a computer controlled electric syringe in which a rubber plug of a cartridge in which a medicinal solution is enclosed is pressed and moved to make a medicinal solution flow into an injection needle and make the medicinal solution discharged from the injection needle. The electric syringe further includes a piston unit; a drive mechanism which transmits a rotative force to the piston unit; a drive motor which transmits a rotative force to the drive mechanism; a motor controller which controls the driving of the drive motor; a stroke sensor which detects the position of the piston of the piston unit; a power supply unit which supplies power to the drive motor, the motor controller; a main processor to which a motor controller, a stroke sensor, and a power supply unit are connected; a main case which covers the piston unit, the drive mechanism, the drive motor, the motor controller, the power supply unit, and the main processor; a cartridge holder socket which is connected to the main case, is provided so that the piston protrudes, and attaches and detaches the cartridge holder into which a cartridge is inserted, and a contact switch which is connected to the main processor, and senses the presence or absence of contact of a human body. The main processor controls the motor controller so as to perform injection at a predetermined injection speed when it is determined that contact has been detected by the contact switch.

Preferably, in the above computer controlled electric syringe, the contact switch is a capacitance type or photo-reflector type contact switch.

The contrivance which enhances precision is made in the capacitance type. Theoretically, the capacitance changes and an oscillation frequency changes as a person touches a sensor unit having an oscillation portion. ON/OFF can be detected by measuring and detecting the amount of change. It was also confirmed by experiment that this contact switch reacts even when rubber gloves are used.

In the photo-reflector type, ON/OFF can be detected by shielding a window hole and measuring and detecting the amount of change of the light. It was also confirmed by experiment that this contact switch reacts even when rubber gloves are used.

These suppress the movement of the needle tip which causes pain, so it is possible to provide a computer controlled electric syringe which is operated simply by touching the contact switch.

Additionally, since a gap portion between the seal portion and the contact switch is eliminated by the adoption of the contact switch, positive sealing becomes possible, and whole washing also become possible.

Additionally, in the electric syringe for a dental treatment anesthetic described in JP-A-2004-130005, an injection speed of a low-speed, a medium-speed, and a high-speed can be selected. However, there is a problem that an operator wants to control the injection speed arbitrarily, for example, according to a part into which the injection needle is inserted. Thus, the computer controlled electric syringe of the invention includes the following invention which solves such problems.

As described with reference to the embodiment, there is provided a computer controlled electric syringe in which a rubber plug of a cartridge in which a medicinal solution is enclosed is pressed and moved to make a medicinal solution flow into an injection needle and make the medicinal solution discharged from the injection needle. The electric syringe further includes a piston unit; a drive mechanism which transmits a rotative force to the piston unit; a drive motor which transmits a rotative force to the drive mechanism; a motor controller which controls the driving of the drive motor; a stroke sensor which detects the position of the piston of the piston unit; a power supply unit which supplies power to the drive motor and the motor controller; a main processor to which a motor controller, a stroke sensor, and a power supply unit are connected; a main case which covers the piston unit, the drive mechanism, the drive motor, the motor controller, the power supply unit, and the main processor; a cartridge holder socket which is connected to the main case, is provided so that the piston protrudes, and attaches and detaches the cartridge holder into which a cartridge is inserted, and a press switch which is connected to the main processor, and outputs a detection signal according to the pressed amount. The main processor controls the motor controller so as to perform injection at an injection speed according to the detection signal output from the press switch.

Preferably, in the above computer controlled electric syringe, the press switch includes a Hall device for detecting the stroke of the pressed amount and outputs a detection signal in accordance with the stroke detected by the Hall device.

In particular, as the start switch, the pushing type press switch is used instead of the contact type. Thus, since the motor controller is controlled so as to perform injection at an injection speed according to the detection signal output from the press switch, stepless and several steps of injections are enabled according to the pressed amount, and an arbitrary injection speed can be selected with one operation.

The stroke of the pressed amount is electrically detected by a Hall device, stepless and several steps of stroke controls are enabled, and the injection speed can be arbitrarily selected with one operation for a stroke. Accordingly, transmission control of stepless or several steps of injection speeds becomes possible.

In the electric syringe for a dental treatment anesthetic described in JP-A-2004-130005, the display part for operation confirmation (operation confirmation lamp) is located on the side opposite to the injection needle. However, since an operator sees the needle tip of an injection needle or an affected part with concentration, there is a problem in that the confirmation of the display part for operation confirmation (operation confirmation lamp) which is located at a position relatively apart from an injection part on the opposite side, and is hard to see depending on an injection part or an angle is neglected. Even during operation, there is a problem in that the operator wants to perform operation confirmation reliably. Thus, the computer controlled electric syringe of the invention includes the following invention which solves such problems.

As described with reference to the embodiment, there is provided a computer controlled electric syringe in which a rubber plug of a cartridge in which a medicinal solution is enclosed is pressed and moved to make a medicinal solution flow into an injection needle and make the medicinal solution discharged from the injection needle. The electric syringe further includes a piston unit; a drive mechanism which transmits a rotative force to the piston unit; a drive motor which transmits a rotative force to the drive mechanism; a motor controller which controls the driving of the drive motor; a stroke sensor which detects the position of the piston of the piston unit; a power supply unit which supplies power to the drive motor and the motor controller; a main processor to which a motor controller, a stroke sensor, and a power supply unit are connected; a main case which covers the piston unit, the drive mechanism, the drive motor, the motor controller, the power supply unit, and the main processor; a cartridge holder socket which is connected to the main case, is provided so that the piston protrudes, and attaches and detaches the cartridge holder into which a cartridge is inserted; and a light-emitting device connected to the main processor. The main case has a transparent, substantially tubular main body, a colored protective portion which covers the outside of the main body, and a display part for operation confirmation which is provided such that the protective painting portion is not formed in the main body. The light emitted from the light-emitting device is made to transmit through the transparent display part for operation confirmation, and is displayed.

Preferably, in the above computer controlled electric syringe, the display part for operation confirmation of the main case goes round in the shape of a ring.

Preferably, in the above computer controlled electric syringe, the main case is formed so that a tip is tapered, and a ring-like display part for operation confirmation with a small cross-sectional area is provided at the tip.

Visibility is enhanced by bringing the position of the display part of operation confirmation as close to an injection part as possible. A circular truncated cone where it is easy to condense light on a tip portion is adopted as the shape near the tip of the main body. Moreover, the condensing efficiency is enhanced by adopting a reflection type as an inner surface, and the display part for operation confirmation is installed at the tip portion near an injection part. The whole periphery of the tip portion of the main body in the shape of a circular truncated cone is made into the display part for operation confirmation. Thereby, the display of the display part for operation confirmation can be confirmed from all directions.

Additionally, although the conventional technique provides the operation indicator 50 which can confirm an injection speed visually by the difference between blinking intervals of a display part, such as an LED, a display part which can confirm an injection amount simultaneously did not exist. The operator needs the information on an injection amount for the operation indicator 50 in addition to the information on an operating state and an injection speed. Thus, the computer controlled electric syringe of the invention includes the following invention which solves such problems.

As described with reference to the embodiment, there is provided a computer controlled electric syringe in which a rubber plug of a cartridge in which a medicinal solution is enclosed is pressed and moved to make a medicinal solution flow into an injection needle and make the medicinal solution discharged from the injection needle. The electric syringe further includes a piston unit; a drive mechanism which transmits a rotative force to the piston unit; a drive motor which transmits a rotative force to the drive mechanism; a motor controller which controls the driving of the drive motor; a stroke sensor which detects the position of the piston of the piston unit; a power supply unit which supplies power to the drive motor and the motor controller; a main processor to which a motor controller, a stroke sensor, and a power supply unit are connected; a main case which covers the piston unit, the drive mechanism, the drive motor, the motor controller, the power supply unit, and the main processor; and a cartridge holder socket which is connected to the main case, is provided so that the piston protrudes, and attaches and detaches the cartridge holder into which a cartridge is inserted. The light-emitting device is a plurality of kinds of light-emitting elements which emit light in different colors, respectively, and the main processor controls ON and OFF of the plurality of kinds of light-emitting elements so as to change the color of the light-emitting elements according to the position of a piston, and makes the light from the light-emitting elements transmit through the display part for operation confirmation, thereby displaying the injection amount of a medicinal solution.

Preferably, in the above computer controlled electric syringe, the injection amount is indicated by a difference in color, and the injection speed is indicated by blinking.

Preferably, in the above computer controlled electric syringe, the main processor makes two or more colors of the light-emitting elements emit light, thereby displaying an injection amount in correspondence with a combined color.

The lighting color of a light-emitting device is changed in correspondence with a distance by which a piston moves forward. Thereby, an operator is able to visually confirm the current injection amount.

Additionally, in this case, blinking according to an injection speed is performed. Thereby, an operator is able to visually confirm the current injection speed.

Accordingly, the injection speed and the injection amount can be simultaneously confirmed, and visibility can be enhanced. Additionally, in this case, it is naturally discerned that injection is being performed.

Additionally, a combined color can be displayed by making light beams from light sources with different colors condense on the tip portion. Light is condensed on a ring-like display part for operation confirmation, thereby providing a combined color. For example, three colors can be used as two types of luminescent color.

Additionally, there is a demand for mounting an information display by a liquid crystal panel. Conventionally, in a stationary computer controlled electric syringe which is connected to a socket which supplies power, there are some which have a liquid crystal display. However, in a cordless computer controlled electric syringe, there is nothing that has an information display by a liquid crystal display panel. Additionally, the information displayed on the information display by the conventional liquid crystal display panel has nothing which displays the residual amount of a medicinal solution intelligibly. Thus, the computer controlled electric syringe of the invention includes the following invention which solves such problems.

As described with reference to the embodiment, there is provided a computer controlled electric syringe in which a rubber plug of a cartridge in which a medicinal solution is enclosed is pressed and moved to make a medicinal solution flow into an injection needle and make the medicinal solution discharged from the injection needle. The electric syringe further includes a piston unit; a drive mechanism which transmits a rotative force to the piston unit; a drive motor which transmits a rotative force to the drive mechanism; a motor controller which controls the driving of the drive motor; a stroke sensor which detects the position of the piston of the piston unit; a power supply unit which supplies power to the drive motor and the motor controller; a main processor to which a motor controller, a stroke sensor, and a power supply unit are connected; a main case which covers the piston unit, the drive mechanism, the drive motor, the motor controller, the power supply unit, and the main processor; and a cartridge holder socket which is connected to the main case, is provided so that the piston protrudes, and attaches and detaches the cartridge holder into which a cartridge is inserted, and an information display which is connected to the main processor, and displays a residual amount with a plurality of bars.

The main processor makes the information display perform a display so that bars are reduced as the residual amount decreases.

In the information display of a liquid crystal panel, in addition to the contents (an injection mode, the kind of cartridge, a sound mode, an injection speed, and the residual amount of the battery) set by an operator, a plurality of bars are displayed in the shape of an anesthetic cartridge. As a result, the change of the residual amount can be intelligibly observed such that the bars in the shape of the anesthetic cartridge decrease depending on the injection amount. Thereby, the injection amount can be visually determined.

Additionally, conventionally, there is a computer controlled electric syringe having a function to inform an operator of the change of the injection amount visually. However, when the presentation position is relatively apart from an injection part, the change of the injection amount may be hard to see merely by visual presentation. Additionally, it maybe hard to see depending on an injection part or an angle. Thus, the computer controlled electric syringe of the invention includes the following invention which solves such problems.

As described with reference to the embodiment, there is provided a computer controlled electric syringe in which a rubber plug of a cartridge in which a medicinal solution is enclosed is pressed and moved to make a medicinal solution flow into an injection needle and make the medicinal solution discharged from the injection needle. The electric syringe further includes a piston unit; a drive mechanism which transmits a rotative force to the piston unit; a drive motor which transmits a rotative force to the drive mechanism; a motor controller which controls the driving of the drive motor; a stroke sensor which detects the position of the piston of the piston unit; a power supply unit which supplies power to the drive motor and the motor controller; a main processor to which a motor controller, a stroke sensor, and a power supply unit are connected; a main case which covers the piston unit, the drive mechanism, the drive motor, the motor controller, the power supply unit, and the main processor; a cartridge holder socket which is connected to the main case, is provided so that the piston protrudes, and attaches and detaches the cartridge holder into which a cartridge is inserted, and a speaker which is connected to the main processor. The main processor makes the speaker perform an output so that sound is changed as the residual amount decreases.

The function to produce a sound whenever a certain amount of injection is performed is added. Additionally, it is expressed by the change of a sound that the injection amount is increasing (the residual amount of a medicinal solution in a cartridge being decreased). (Example: whenever the injection amount approaches 0.6 ml, a sound is changed). In this way, an operator is informed of the change of the injection amount in real time with sound.

Additionally, in order to confirm that a needle has not erroneously entered a blood vessel at the time of injection, an aspiration operation may be performed (back aspiration). However, in the aspiration operation which uses a piston which has an O-ring-shaped rubber which adheres tightly to the inner wall surface of a cartridge installed at the tip portion thereof, since the cartridge itself will move back with the piston and the cartridge will be separated from the needle, aspiration may not be performed. Thus, the computer controlled electric syringe of the invention includes the following invention which solves such problems.

As described with reference to the embodiment, there is provided a computer controlled electric syringe in which a rubber plug of a cartridge in which a medicinal solution is enclosed is pressed and moved to make a medicinal solution flow into an injection needle and make the medicinal solution discharged from the injection needle. The electric syringe further includes a piston unit; a drive mechanism which transmits a rotative force to the piston unit; a drive motor which transmits a rotative force to the drive mechanism; a motor controller which controls the driving of the drive motor; a stroke sensor which detects the position of the piston of the piston unit; a power supply unit which supplies power to the drive motor and the motor controller; a main processor to which a motor controller, a stroke sensor, and a power supply unit are connected; a main case which covers the piston unit, the drive mechanism, the drive motor, the motor controller, the power supply unit, and the main processor; and a cartridge holder socket which is connected to the main case, is provided so that the piston protrudes, and attaches and detaches the cartridge holder into which a cartridge is inserted. The cartridge holder includes an engaging portion which enters a concave surface of a cartridge and locks and fixes the cartridge.

In this way, a cartridge holder having a protruding portion with a spring property caught in a groove portion provided near an aluminum cap portion of a cartridge has been developed. A cartridge is fixed to the cartridge holder at a predetermined position. As a result, a cartridge holder is obtained in which a cartridge for an anesthetic, etc. continues to be fixed to a predetermined position, even in the aspiration which uses a piston which has an O-ring-shaped rubber which adheres tightly to the inner wall surface of a cartridge.

Additionally, in order to confirm that a needle has not erroneously entered a blood vessel at the time of injection, there is a demand for performing an aspiration operation with a simple construction. Thus, the computer controlled electric syringe of the invention includes the following invention which solves such problems.

As described with reference to the embodiment, there is provided a computer controlled electric syringe in which a rubber plug of a cartridge in which a medicinal solution is enclosed is pressed and moved to make a medicinal solution flow into an injection needle and make the medicinal solution discharged from the injection needle. The electric syringe further includes a piston unit; a drive mechanism which transmits a rotative force to the piston unit; a drive motor which transmits a rotative force to the drive mechanism; a motor controller which controls the driving of the drive motor; a stroke sensor which detects the position of the piston of the piston unit; a power supply unit which supplies power to the drive motor and the motor controller; a main processor to which a motor controller, a stroke sensor, and a power supply unit are connected; a main case which covers the piston unit, the drive mechanism, the drive motor, the motor controller, the power supply unit, and the main processor; a cartridge holder socket which is connected to the main case, is provided so that the piston protrudes, and attaches and detaches the cartridge holder into which a cartridge is inserted, and an aspiration switch which is connected to the main processor. The main processor controls the motor controller so as to separate the tip of a piston from a rubber plug of a cartridge at high speed according to the depression of the aspiration switch, so the electric syringe is able to confirm the presence or absence of inflow of blood into the cartridge by the negative pressure to a medicinal solution which is caused with the expansion of the medicinal solution and the rubber plug.

When the aspiration switch is pushed, a piston moves back by a distance required for aspiration (for example, the piston is returned at 1.8 mm/sec), and the presence or absence of inflow of blood can be confirmed. Thereby, it can be confirmed whether or nor the needle has erroneously entered a blood vessel.

Additionally, there is a demand for use as an application where a medicinal solution is injected other than a dental anesthetic cartridge. However, in the conventional electric syringe, a medicinal solution cannot be aspirated into an empty cartridge and injected. Thus, the computer controlled electric syringe of the invention includes the following invention which solves such problems.

As described with reference to the embodiment, there is provided a computer controlled electric syringe in which a rubber plug of a cartridge in which a medicinal solution is enclosed is pressed and moved to make a medicinal solution flow into an injection needle and make the medicinal solution discharged from the injection needle. The electric syringe further includes a piston unit; a drive mechanism which transmits a rotative force to the piston unit; a drive motor which transmits a rotative force to the drive mechanism; a motor controller which controls the driving of the drive motor; a stroke sensor which detects the position of the piston of the piston unit; a power supply unit which supplies power to the drive motor and the motor controller; a main processor to which a motor controller, a stroke sensor, and a power supply unit are connected; a main case which covers the piston unit, the drive mechanism, the drive motor, the motor controller, the power supply unit, and the main processor; a cartridge holder socket which is connected to the main case, is provided so that the piston protrudes, and attaches and detaches the cartridge holder into which a cartridge is inserted, and an aspiration switch which is connected to the main processor. An engaging portion is provided at the tip of the piston, and the main processor controls the motor controller so as to make the tip of the piston locked to a rubber plug of an empty cartridge according to the depression of the aspiration switch, and pull in the rubber plug of the empty cartridge with the piston, when the amount of aspiration is preset, and makes a medicinal solution of the preset amount aspirated into the empty cartridge by the negative pressure which is caused with the pull-in of the rubber plug of the empty cartridge.

A predetermined amount of medicinal solution is aspirated as the piston moves back by a set distance according to the depression of the aspiration switch after the amount of aspiration is preset. A medicinal solution can be aspirated into an empty cartridge, and administration of the aspirated medicinal solution becomes possible.

The computer controlled electric syringe of the invention aspirates a medicinal solution into an empty cartridge, for example, when a power button is pushed while the aspiration switch is pushed.

Additionally, there is no electric syringe in which the kind of cartridge to be used is switched only by a button operation. There is a demand for switching the kind of cartridge to be used only by a button operation and improving usability for an operator. Thus, the computer controlled electric syringe of the invention includes the following invention which solves such problems.

As described with reference to the embodiment, there is provided a computer controlled electric syringe in which a rubber plug of a cartridge in which a medicinal solution is enclosed is pressed and moved to make a medicinal solution flow into an injection needle and make the medicinal solution discharged from the injection needle. The electric syringe further includes a piston unit; a drive mechanism which transmits a rotative force to the piston unit; a drive motor which transmits a rotative force to the drive mechanism; a motor controller which controls the driving of the drive motor; a stroke sensor which detects the position of the piston of the piston unit; a power supply unit which supplies power to the drive motor and the motor controller; a main processor to which a motor controller, a stroke sensor, and a power supply unit are connected; a main case which covers the piston unit, the drive mechanism, the drive motor, the motor controller, the power supply unit, and the main processor; a cartridge holder socket which is connected to the main case, is provided so that the piston protrudes, and attaches and detaches the cartridge holder into which a cartridge is inserted; and a cartridge setting switch connected to the main processor. The cartridge holder is a common cartridge holder which holds any one cartridge of two types of cartridges which are different in length, and when the cartridge holder is set in the computer controlled electric syringe, and any one of two types of cartridges which are different in length is selected by pushing the cartridge setting switch, the main processor determines whether an output value from a stroke sensor coincides with a preset registered value of the position of the cartridge, controls the motor controller so as to move the piston to another position at the time of non-coincidence, and controls the motor controller so as to stop the piston at the time of coincidence.

In order to mount, for example, 1.8 mL and 1.0 mL cartridges which are different in length, a piston moves automatically to a suitable position only by a switch operation. Specifically, position confirmation is performed by interlocking between the piston and a position sensor. The switching function of a cartridge becomes possible.

According to the computer controlled electronic syringe 1, since miniaturization and weight reduction are realized, pen grip becomes possible. Since an operator actuates the start button with a finger, usability is improved.

Additionally, exposure of a charging terminal is eliminated by adopting the noncontact power transmission module, soaking in a disinfectant solution can be made by making the main body fully waterproofed, and cleaning and sterilization are possible (fully waterproof) by being soaked in a disinfectant.

The present invention can be applied to a computer controlled electric syringe for injecting a medicinal solution for medical treatment or dental treatment.

Although the embodiment according to the present invention has been described above, the present invention is not limited to the above-mentioned embodiment but can be variously modified. Constituent components disclosed in the aforementioned embodiment may be combined suitably to form various modifications. For example, some of all constituent components disclosed in the embodiment may be removed, replaced, or may be appropriately combined with other components.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A computer controlled electric syringe comprising:
a piston unit comprising:
a piston comprising a first end, a second end and a hollow portion communicating with an opening formed at the first end, the piston being configured to press and move a rubber plug of a cartridge, in which a medicinal solu- tion is enclosed, by the second end to discharge the medicinal solution from the cartridge through an injection needle;
a ball screw comprising a screw shaft and a nut portion that is screwed into the screw shaft, the screw shaft being loosely inserted into the hollow portion of the piston through the opening, the nut portion being coupled to the piston;
a screw shaft supporting portion rotatably supporting the screw shaft of the ball screw;
a rotation preventing portion configured to prevent the nut portion of the ball screw from being rotated; and
a piston supporting portion supporting the piston to be movable in an axial direction of the screw shaft along with the nut portion by the rotation of the screw shaft.

2. The computer controlled electric syringe according to claim 1 further comprising:
a drive motor;
a drive mechanism configured to transmit a rotative force output from the drive motor to the screw shaft of the ball screw of the piston unit;
a motor controller configured to control the drive motor;
a stroke sensor configured to detect a position of the piston of the piston unit;
a power supply unit configured to supply power to the drive motor, the motor controller, and the stroke sensor;
a main processor connected to the motor controller, the stroke sensor, and the power supply unit;
a main case covering the piston unit, the drive mechanism, the drive motor, the motor controller, the power supply unit, the stroke sensor, and the main processor; and
a cartridge holder socket connected to the main case and configured to allow the piston to pass through while maintaining water-tightness, the cartridge holder socket being configured to receive a cartridge holder into which the cartridge is inserted.

3. The computer controlled electric syringe according to claim 2,
wherein the power supply unit comprises a noncontact power transmission module, a battery charge circuit connected to the noncontact power transmission module, and a battery connected to the battery charge circuit, and
wherein the noncontact power transmission module is configured to receive electric power that is externally supplied in noncontact and to charge the battery with the electric power.

4. The computer controlled electric syringe according to claim 2 further comprising:
a contact switch connected to the main processor and detects whether a human body is in contact,
wherein the main processor is configured to control the motor controller so as to perform injection at a predetermined injection speed when determined that the contact of the human body is detected by the contact switch.

5. The computer controlled electric syringe according to claim 4,
wherein the contact switch is of a capacitance type contact switch or a photo-reflector type contact switch.

6. The computer controlled electric syringe according to claim 2 further comprising:
a press switch connected to the main processor and outputs a detection signal according to a pressed amount,
wherein the main processor is configured to control the motor controller so as to perform injection at an injection speed that is changed in accordance with the detection signal output from the press switch.

7. The computer controlled electric syringe according to claim 6,
wherein the press switch comprises a Hall device for detecting a stroke of the pressed amount and outputs the detection signal in accordance with the stroke detected by the Hall device.

8. The computer controlled electric syringe according to claim 2 further comprising:
a light-emitting device connected to the main processor,
wherein the main case comprises: a transparent, substantially tubular main body; a colored protective portion that covers the main body; and an operation indicator configured on the main body at a portion excluding the colored protective portion, and
wherein the operation indicator outputs light emitted from the light-emitting device therethrough for visually recognizing an operational status of the computer controlled electric syringe.

9. The computer controlled electric syringe according to claim 8,
wherein the operation indicator is arranged around the main body to have a ring shape.

10. The computer controlled electric syringe according to claim 9,
wherein the main case is formed to have a shape tapered toward the cartridge holder socket, and
wherein the operation indicator is arranged at a position near the cartridge holder socket where a diameter of the main case is small.

11. The computer controlled electric syringe according to claim 8,
wherein the light-emitting device comprises a plurality of light-emitting elements that emit light in different colors, and
wherein the main processor is configured to control the light-emitting elements so as to change the color of the light in accordance with a position of the piston, and to notify a user an injection amount of the medicinal solution.

12. The computer controlled electric syringe according to claim 11,
wherein the main processor is configured to control the light-emitting elements to blink in accordance with an injection speed of the medicinal solution.

13. The computer controlled electric syringe according to claim 11,
wherein the main processor is configured to control the light-emitting elements to be simultaneously turned ON so as to output light having a combined color in accordance with the injection amount of the medicinal solution.

14. The computer controlled electric syringe according to claim 2 further comprising:
an information display connected to the main processor and displays residual amount of the medicinal solution of a cartridge with a plurality of bars,
wherein the main processor is configured to control the information display to display the bars in accordance with the residual amount of the medicinal solution.

15. The computer controlled electric syringe according to claim 2 further comprising:
a speaker connected to the main processor,
wherein the main processor is configured to control the speaker to output a sound that is changed in accordance with a residual amount of the medicinal solution of the cartridge.

16. The computer controlled electric syringe according to claim 2,
   wherein the cartridge holder comprising a protruding portion engages with a concave surface formed on the cartridge to retain the cartridge.

17. The computer controlled electric syringe according to claim 2 further comprising:
   an aspiration switch connected to the main processor,
   wherein the main processor is configured to control the motor controller so as to separate the second end of the piston from the rubber plug of the cartridge at high speed when the aspiration switch is pressed, and to aspiration blood into the cartridge by negative pressure applied to the medicinal solution by an expansion of the medicinal solution and the rubber plug.

18. The computer controlled electric syringe according to claim 2 further comprising:
   an aspiration switch connected to the main processor,
   wherein the piston is provided with an engaging portion at the second end, the engaging portion being configured to be engaged with the rubber plug of an empty cartridge, and
   wherein the main processor is configured to control the motor controller so as to pull in the rubber plug of the empty cartridge when the aspiration switch is pressed, and to aspirate the medicinal solution into the empty cartridge by negative pressure caused by pulling in the rubber plug.

19. The computer controlled electric syringe according to claim 2,
   wherein the cartridge holder is configured as a common cartridge holder capable to hold any one cartridge of a plurality of types of cartridges which are different in length,
   wherein the computer controlled electric syringe further comprises a cartridge setting switch for selecting one of the cartridges to be set in the cartridge holder, the cartridge setting switch being connected to the main processor, and
   wherein the main processor is configured to determine whether an output value from the stroke sensor coincides with a preset registered value of a position of the cartridge, to control the motor controller so as to move the piston to another position when the output value from the stroke sensor does not coincide with the preset registered value, and to control the motor controller so as to stop the piston when the output value from the stroke sensor coincides with the preset registered value.

20. A syringe comprising:
   a piston having an opening communicating to a hollow interior portion;
   a ball screw comprising a screw shaft which has a threaded outer periphery, the screw shaft being insertable into the hollow portion of the piston though the opening of the piston;
   a nut portion which rotates relative to the screw shaft, and is threaded to the screw shaft and coupled to the piston at the opening of the piston;
   a screw shaft supporting portion rotatably supporting the screw shaft of the ball screw, at an end of the piston nearest the opening;
   a rotation preventing portion comprising a protruding portion and a sliding passage, the protruding portion being fixed to the nut portion and the sliding passage being formed in a bottom base, the protruding portion being configured to move only inside the sliding passage such that the nut portion and the piston, coupled to the nut portion, move only in an axial direction;
   a piston supporting portion which supports the piston so that the piston is movable in the axial direction, and which is positioned at an opposite end of the piston than the opening;
   a cartridge holder socket having a hollow interior in axial alignment with the piston; and
   a cartridge holder being detachable connected to the cartridge holder socket.

* * * * *